(12) United States Patent
Jablonski et al.

(10) Patent No.: US 8,243,271 B2
(45) Date of Patent: Aug. 14, 2012

(54) METHODS FOR FABRICATING ANALYTICAL SUBSTRATES USING METALLIC NANOPARTICLES

(75) Inventors: Gregory Jablonski, Yardley, PA (US); Michael Mastropietro, Bridgewater, NJ (US)

(73) Assignee: PChem Associates, Inc., Bensalem, PA (US)

( * ) Notice: Subject to any disclaimer, the term of this patent is extended or adjusted under 35 U.S.C. 154(b) by 383 days.

(21) Appl. No.: 12/714,430

(22) Filed: Feb. 26, 2010

(65) Prior Publication Data
US 2010/0245814 A1    Sep. 30, 2010

Related U.S. Application Data

(60) Provisional application No. 61/155,909, filed on Feb. 26, 2009.

(51) Int. Cl.
*G01J 3/44* (2006.01)
(52) U.S. Cl. ....................................... 356/301
(58) Field of Classification Search ................... 356/301
See application file for complete search history.

(56) References Cited

U.S. PATENT DOCUMENTS

2006/0215154 A1* 9/2006 Chan et al. ................... 356/244
2011/0026019 A1* 2/2011 Tyagi et al. ................... 356/301

OTHER PUBLICATIONS

Suzuki et al., "Heat-induced morphological control of gold nanoparticle films for surface-enhanced Raman scattering (SERS) measurements", Dec. 15, 2005, Elsevier, pp. 388-394.*
Figueroa et al., "Development of surface-enhanced Raman scattering (SERS) substrates using nanoparticle-based printing inks", SPIE, vol. 6866, pp. 1-6.*

* cited by examiner

*Primary Examiner* — Kara E Geisel
(74) *Attorney, Agent, or Firm* — Cantor Colburn LLP

(57) ABSTRACT

An analytical substrate for amplifying Raman signals by a factor greater than 10,000, or by a factor less than 1,000,000. The analytical substrate is fabricated by depositing a film on the substrate and heating the substrate to a temperature less than 100 degrees Celsius for a period of time less than 30 seconds. The film can comprise a metallic nanoparticle dispersion that can further comprise a population of metallic nanoparticles. In some instances, the metallic nanoparticles have an average cross-sectional dimension in a range of about 1 nm to about 100 nm. In other instances each nanoparticle comprises at least one ligand bound to a surface of the nanoparticle, where the ligand comprises a heteroatom head group bound to the nanoparticle surface and a tail bound to the heteroatom head group.

20 Claims, 11 Drawing Sheets

Log-Log Plot of Perimeter as a Function of Area for particles.
Inset Shows Printed Metal Microstructure.

SERS spectrum for β-Carotene extracted from a carrot.
The intensity scale is in arbitrary units.

SERS spectrum of lysate of a genetically modified 293 human epithelial kidney cell line. The intensity scale is in arbitrary units.

METHODS FOR FABRICATING ANALYTICAL SUBSTRATES USING METALLIC NANOPARTICLES

RELATED APPLICATIONS

This U.S. patent application claims priority to U.S. Provisional Patent Application Ser. No. 61/155,909, filed on Feb. 26, 2009, the disclosure of which is considered part of the disclosure of this application and is herein incorporated by reference in its entirety.

FUNDING ACKNOWLEDGEMENT

A portion of the research for the methods and compositions described in this disclosure, was supported by the Commonwealth of Pennsylvania's Ben Franklin Technology Development Authority through the Ben Franklin Technology Partners of Southeastern Pennsylvania as fiscal agents for the Nanotechnology Institute.

FIELD OF THE DISCLOSURE

The present disclosure relates to analytical substrates. In particular, this disclosure is directed towards analytical substrates fabricated by applying metallic nanoparticles to a substrate so that the substrate can act as a Raman signal amplifier.

BACKGROUND OF THE INVENTION

Raman scattering can result from an inelastic collision of a photon with atoms or molecules. During elastic collisions (Rayleigh scattering), an atom can be excited from a ground state to a higher energy state, and can then relax back to the original ground state upon which the atom emits a photon at the same frequency as light incident on the atom. However, during an inelastic collision, an excited atom may relax to a vibrationally excited state rather than the ground state upon which a scattered photon can be emitted (Stoke's line) with energy lower than the incident photon. If the incident photon interacts with an already vibrationally excited molecule, the scattered photon can be emitted with higher energy (Anti-Stokes line) than the incident photon. Illustrated in FIG. 4 is an embodiment of a representation of the Raman spectrum.

Raman spectroscopy can give information about the characteristic vibrational states of the chemical bonds of the molecules being studied. This molecular level specificity has made Raman spectroscopy a widely used spectroscopic tool for the determination of molecular structure and for compound identification. As such, this technique is useful for a variety of applications that require the detection of biologically significant molecules such as toxins and disease biomarkers.

Despite the inherent advantages of using Raman Spectroscopy, its usage has been somewhat limited because it is an inefficient analysis technique. Raman spectroscopy has a small scatter cross section compared to Fluorescence spectroscopy ($10^{-30}$ cm² per molecule when compared to $10^{-16}$ cm² for fluorescence.) Thus, Raman spectroscopy often cannot be used to analyze compounds of biological significance due to the generally low concentration of analytes in biological samples. There are, however, ways to greatly enhance the Raman signal by using particularly structured metallic (e.g. Ag, Au, and Cu) substrates, where the metallic structure enhances the Raman scattering. Surface Enhanced Raman Scattering (SERS) was first reported in 1974 by Fleischmann. M. Fleischmann, P. J. Hendra, and A. J. McQuillan, "Raman spectra of pyridine adsorbed at a silver electrode," *Chemical Physics Letters* 26, 163-166 (1974). Fleischmann observed a large enhancement of Raman signals of pyridine molecules adsorbed on electrochemically roughened silver electrodes. SERS amplification factors (AF) of $10^6$~$10^{16}$ have been achieved using a wide range of SERS substrates, thus the SERS enhancement effect has made Raman spectroscopy an increasingly important analytical tool in the biological sciences.

Typical SERS substrates are fabricated using methods that result in noble metal nanostructures stochastically distributed over a substrate surface, e.g. electrochemically roughened electrodes, sputtered films, chemically etched films, electroless deposited films, and colloidal metal particles. Another way to obtain large amplification in Raman scattering can be to place a substrate in close proximity of a sharp metallic tip. Although SERS amplifications of $10^3$-$10^5$ have been reported using such substrates, these substrates are often not reproducible.

Still other SERS substrates are created by depositing colloidal silver particles on quartz/glass substrates using standard wet chemistry. These fabrication methods can typically result in a monolayer of nanoparticles. Using a process such as depositing the particles on quartz or glass using standard wet chemistry can create hot spots during the colloidal preparation.

SERS substrates can also be fabricated by controlling the pattern of the nanostructures on a substrate using electron-beam lithography. Substrates created using this method are now commercially available and manufactured by D3 Technologies Ltd, Glasgow, UK. These substrates are fabricated using a multi-step process that results in substrates which are quite expensive (e.g. $75-$125/substrate.) These substrates are also usually small in size (e.g. 4 mm by 4 mm.) There is no easy way to commercialize the method described above because SERS substrates created using the nano-lithographic process can have the following limitations: they are expensive to produce; the equipment required to produce them is sophisticated and expensive; and it is difficult to produce substrates that have a size which exceeds approximately a centimeter square.

There exists a need for inexpensive methods and compositions for fabricating analytical substrates for use in SERS and substrates that reliably amplify incident photons emitted by a spectrometer. In particular there exists a need for cost effective SERS substrate fabrication methods that produce analytical substrates that meet a particular performance measurement.

SUMMARY OF THE INVENTION

In one embodiment, the present disclosure describes metallic nanoparticle structures that are created using a process in which metallic nanoparticle-based inks are deposited onto a substrate and the deposited metallic nanoparticle-based inks are allowed to at least partially cure on the substrate thereby creating metallic nanoparticle structures. The resultant substrate and metallic nanoparticle structure combination can, in some embodiments, be used in Raman spectroscopy to identify many different chemical and biological species. The presence of the metallic nanoparticle structures on the substrate transforms the substrate into an amplifier that when used in Raman spectroscopy, enhances the sensitivity of the Raman signal by several orders of magnitude. This enhancement, which is achieved by the complex interaction of the Raman signal with the deposited and at least partially cured metallic nanoparticles allows large area, inexpensive sample substrates to be used to increase the detection sensitivity and speed of analysis of the Raman spectroscopic method. In some embodiments, the substrates can be further doped or biased to enhance the collection of the sample of interest. In still other embodiments, either large substrates or a large number of substrates can be created and utilized to insure the accuracy of the method and to significantly increase the detection sensitivity and reduce the time to complete the analysis. The methods and compositions described in the present disclosure significantly reduce the cost of producing such large substrates or large number of substrates because they are less resource intensive.

In one aspect, described herein is an embodiment of a method for fabricating a substrate that amplifies Raman signals. The method includes depositing a film comprising a metallic nanoparticle dispersion, on a substrate. The metallic nanoparticle dispersion can include a metallic nanoparticle population. The substrate can then be heated to a temperature less than 100 degrees Celsius for a period of time less than 30 seconds to generate a substrate for amplifying a Raman signal by a factor greater than 10,000.

In one embodiment, the metallic nanoparticles of the metallic nanoparticle population can have an average cross-sectional dimension in a range of about 1 nm to about 100 nm.

In another embodiment, each metallic nanoparticle of the metallic nanoparticle population can include at least one ligand bound to a surface of the nanoparticle, the ligand comprising a heteroatom head group bound to the nanoparticle surface and a tail bound to the heteroatom head group.

In still another embodiment, the resulting substrate can amplify the Raman signal by a factor less than 1,000,000.

The substrate, in some embodiments, can be heated to a temperature less than 80 degrees Celsius.

In one embodiment, the substrate is heated to generate a substrate comprising a network of metallic nanoparticle structures that further comprise hot spots.

In still other embodiments, the substrate can be heated to a temperature less than 50 degrees Celsius.

The substrate, in some embodiments, can be a paper substrate.

In one embodiment, the substrate can be heated for a period of time less than 15 seconds.

In another aspect, described herein is an analytical substrate that amplifies Raman signals, where in one embodiment the analytical substrate includes a substrate. The analytical substrate can further include at least one metallic nanoparticle structure that is fabricated by depositing a metallic nanoparticle dispersion comprising a metallic nanoparticle population, on the substrate. The substrate can then be heated to a temperature less than 140 degrees Celsius for a period of time less than 60 seconds. The resulting at least one metallic nanoparticle structure can amplify a Raman signal by a factor greater than 10,000.

In one embodiment, each metallic nanoparticle of the metallic nanoparticle population can have an average cross-sectional dimension in a range of about 1 nm to about 100 nm.

In another embodiment, each metallic nanoparticle of the metallic nanoparticle population can have at least one ligand bound to a surface of the nanoparticle, the ligand comprising a heteroatom head group bound to the nanoparticle surface and a tail bound to the heteroatom head group.

The nanoparticle population, in some embodiments, includes a particle agglomerate comprised of two or more individual nanoparticles, nanoparticle floc comprised of two or more individual nanoparticles, or any combination thereof. In one embodiment, the ratio, by weight, of the population of individual metallic nanoparticles to particle agglomerate can be in the range of from about 1:99 to 99:1. In another embodiment, the ratio, by weight, of the population of individual metallic nanoparticles to particle floc can be in the range of from about 1:99 to 99:1. In still another embodiment, the nanoparticle agglomerate has an average cross-sectional dimension in the range of from about 100 nm to about 10000 nm, while in another embodiment the nanoparticle floc has an average cross-sectional dimension in the range of from about 100 nm to about 10000 nm.

In some embodiments, the substrate is paper.

In another embodiment, the at least one metallic nanoparticle structure amplifies the Raman signal by a factor less than 1,000,000.

BRIEF DESCRIPTION OF THE DRAWINGS

The following figures depict certain illustrative embodiments of the methods and compositions described herein, where like reference numerals refer to like elements. Each depicted embodiment is illustrative of the methods and compositions and not limiting.

DETAILED DESCRIPTION OF THE DRAWINGS

Figure 1A:
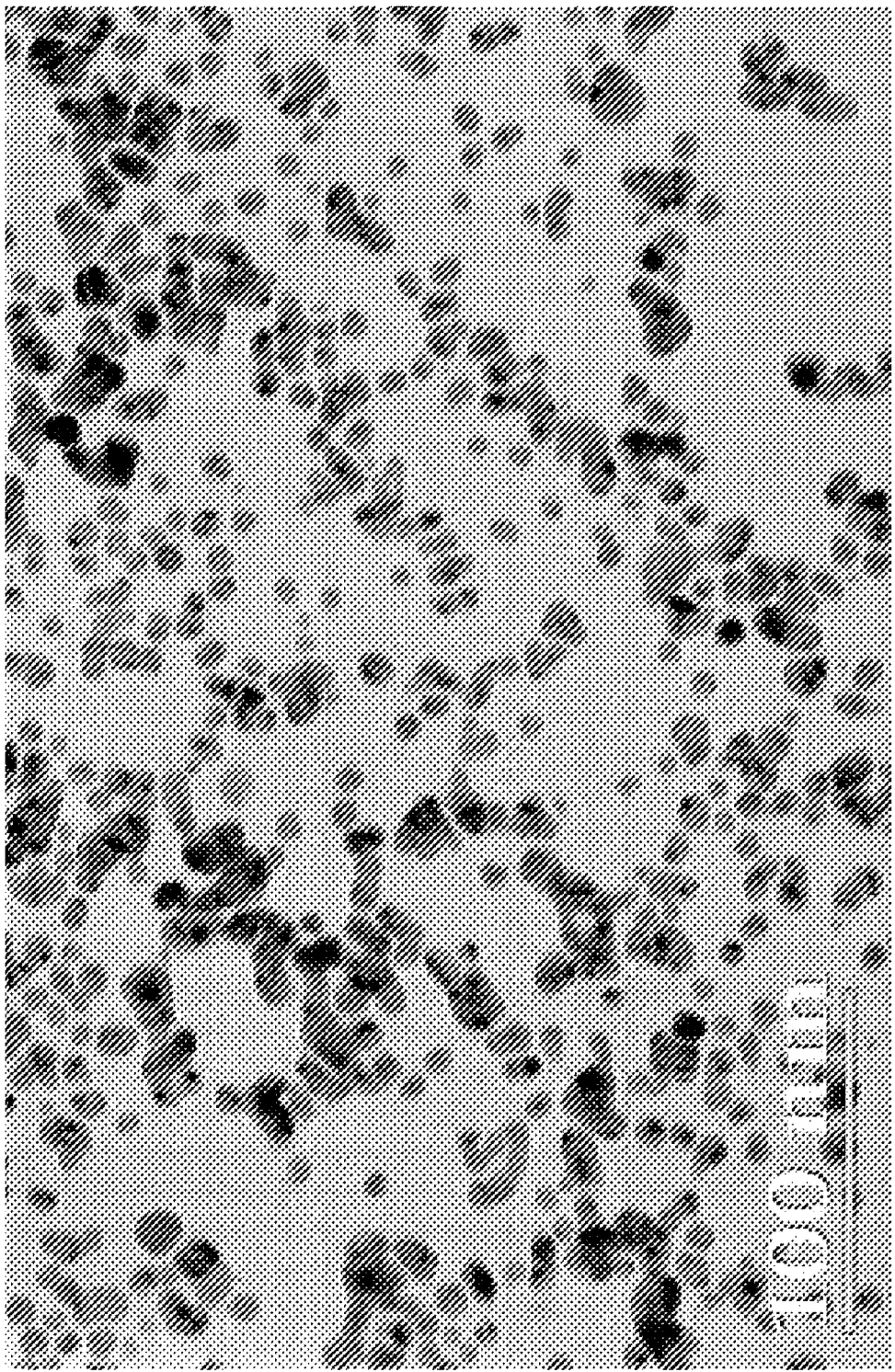
FIG. 1A depicts an embodiment of a transmission electron microscope ("TEM") micrograph of silver nanoparticles synthesized by the present invention.

For purposes of reading the description of the various embodiments below, the following descriptions of the sections of the specification and their respective contents may be helpful:

Section A describes embodiments of methods for synthesizing metallic nanoparticles and metallic nanoparticle compositions; and Section B describes embodiments of methods for creating analytical substrates that can be used, for example, in Surface Enhanced Raman Spectroscopy (SERS.)

Section A: Metallic Nanoparticle Compositions and Methods for Synthesizing Metallic Nanoparticle Compositions Terms As used herein, the term "aqueous" means containing water.

As used herein, the term "bonding" means covalently bonded, ionically bonded, hydrogen bonded, coordinate bonded, and the like.

As used herein, the term "tail" means a straight, branched, or cyclic chain of carbon atoms, wherein the chain may be aliphatic, and wherein the chain may have one or more additional groups bound to one or more of its member carbon atoms. An example would be a chain of aliphatic carbon atoms with an alcohol group attached to one of the chain members.

As used herein, the term "heteroatomic head group" means a group including at least one atom wherein at least one atom within the group is atom other than carbon. Examples include nitrogen, sulfur, or oxygen.

As used herein, the term "cohesive" means united as a single entity and resisting separation.

As used herein, the term "complexing" means forming coordinating bonds with a metal atom or ion.

As used herein, the term "ligand" can mean a molecule or a molecular group that binds to another chemical entity to form a larger complex. Examples include a molecular group that becomes bound to a metal or metal ion by a coordinate covalent bond through donating electrons from a lone electron pair of the ligand into an empty metal electron orbital.

As used herein, the term "agglomeration" means two or more particles reversibly clustered together, wherein the surfaces of the particles do not come into contact with one another.

As used herein, the term "floc" can mean two or more particles reversibly clustered together, wherein the surfaces of the particles do not come into contact with one another.

As used herein, the term "bulk resistivity" can mean the inherent resistivity of a material that makes up a specified object. For example, the bulk resistivity of a ingot made of silver would be the inherent conductivity of silver. As another example, the bulk resistivity of an ingot made of an alloy comprising silver and gold would be the inherent conductivity of the silver and gold alloy.

As used herein, the terms "aggregate", "aggregation", and similar forms can mean a unified structure comprised of two or more particles irreversibly fused, connected, or necked together.

Compositions of the present invention can include a population of metallic nanoparticles dispersed in an aqueous medium, wherein at least a portion of the population comprising individual metallic nanoparticles characterized as having an average cross-sectional dimension in the range of from about 1 nm to about 100 nm; and, wherein each of the nanoparticles can include at least one ligand bound to its surface, the ligand comprising a heteroatom head group bound to the nanoparticle surface and a tail bound to the heteroatom head group.

Nanoparticle populations can comprise a particle agglomerate that includes two or more individual nanoparticles, a nanoparticle floc that includes two or more individual nanoparticles, or any combination thereof. The ratio, by weight, of the population of individual metallic nanoparticles to particle agglomerate is contemplated as being in the range of from about 1:99 to 99:1, and the ratio, by weight, of the population of individual metallic nanoparticles to particle floc is contemplated as being in the range of from about 1:99 to 99:1.

In certain embodiments, a nanoparticle agglomerate has an average cross-sectional dimension in the range of from about 100 nm to about 10000 nm; a nanoparticle floc has an average cross-sectional dimension in the range of from about 100 to about 10000 nm.

An individual metallic nanoparticle may include silver, copper, gold, zinc, cadmium, palladium, iridium, ruthenium, osmium, rhodium, platinum, iron, nickel, cobalt, indium, silver oxide, copper oxide, gold oxide, zinc oxide, cadmium oxide, palladium oxide, iridium oxide, ruthenium oxide, osmium oxide, rhodium oxide, platinum oxide, iron oxide, nickel oxide, cobalt oxide, indium oxide, or any combination thereof.

It is contemplated that the ligand tail can include from about 1 to about 20 carbon atoms. The tail can comprise a straight-chain segment, a branched segment, a cyclic segment, or any combination thereof, and can further comprise an aliphatic chain, an acid group, an alcohol group, an amphophilic group, an amine group, and the like, or any combination thereof.

Suitable heteroatom head groups can include oxygen, sulfur, nitrogen, and the like.

The aqueous medium can include water, and it is envisioned that the aqueous medium can further include one or more polar organic solvents, one or more non-polar organic solvents, or any combination thereof. A suitable polar organic solvent comprises an alcohol, a polyol, a glycol ether, 1-methylpyrolidinone, pyridine, methylethylketone, or any combination thereof. A suitable non-polar organic solvent comprises tetrahydrofuran, toluene, xylene, a C-sub-5 ($C_5$) to C-sub-14 ($C_{14}$) branched paraffin, a C-sub-5 ($C_5$) to C-sub-14 ($C_{14}$) unbranched paraffin, N,N-dimethyl formamide, or any combination thereof.

The aqueous medium is typically capable of solvating the metallic salt in a range of from about 10 grams/liter to about 600 grams/liter, or even 50 to 200, or even 80 to 120.

In some embodiments, the nanoparticles are present in the range of from about 0.5 wt % to about 70 wt %, the ligand can be present in a range of from about 0.5 wt % to about 75 wt %, and the medium can be present in a range of from about 30 to about 98 wt %.

In other embodiments, the composition is capable of forming a cohesive structure of less than about 10 micrometers in thickness following curing at a temperature of less than about 110 degrees Celsius for less than about 90 seconds. The structure suitably has a resistivity in the range of from about 2 times to about 15 times the bulk resistivity of the corresponding metals present in the composition.

Compositions can also include a metallic nanoparticle mixture capable of forming a cohesive structure of less than about 10 micrometers in thickness following curing at a temperature of less than about 110 degrees Celsius for less than about 60 seconds, or capable of forming a cohesive structure of less than about 5 micrometers in thickness following curing at a temperature of less than about 140 degrees Celsius for less than about 15 seconds, or capable of forming a cohesive structure of less than about 2 micrometers in thickness following curing at a temperature of less than about 110 degrees Celsius for less than about 10 seconds, or capable of forming a cohesive structure of less than about 2 micrometers in thickness following curing at a temperature of less than about 140 degrees Celsius for less than about 5 seconds, wherein the cohesive structure has a resistivity in the range of from about 2 times to about 15 times the bulk resistivity of the corresponding metal in the composition.

Suitable mixtures can include a population of metallic nanoparticles, a ligand, an aqueous medium, or any combination thereof.

In some embodiments, the metallic nanoparticle populations can include individual nanoparticles, a particle agglomerate comprised of two or more individual nanoparticles, a particle floc comprised of two or more individual nanoparticles, or any combination thereof. The ratio, by weight, of the population of individual metallic nanoparticles to particle agglomerate can be in a range of from about 1:99 to 99:1, and the ratio, by weight, of the population of individual metallic nanoparticles to particle floc can be in a range of from about 1:99 to 99:1. In other embodiments, substantially all of the nanoparticles are agglomerated. In still other embodiments, substantially all of the nanoparticles are discrete individual nanoparticles.

In some embodiments of the invention, individual metallic nanoparticles can have an average cross-sectional dimension in the range of from about 1 nm to about 100 nm; or even from about 5 nm to about 30 nm, or even from about 10 nm to about 20 nm. Particle size can be measured using an acoustic attenuation spectroscopy method substantiated by transmission electron microscopy. Particle agglomerates have an average cross-sectional dimension of at least about 2 nm, or even at least about 20 nm, or even at least about 200 nm, or in the range of from about 100 nm to about 10000 nm; and particle flocs have an average cross-sectional dimension in the range of from about 100 nm to about 10000 nm. Individual metallic nanoparticles and ligands are as described elsewhere herein; ligands can be characterized as bound to a surface of one or more metallic nanoparticles by a heteroatom head group so as to give rise to one or more metallic nanoparticles stabilized against irreversible aggregation.

The aqueous medium of these compositions can comprise water, and can further comprise one or more polar organic solvents, one or more non-polar organic solvents, or any combination thereof. The aqueous medium is typically capable of solvating the metallic salt in a range of from about 10 grams/liter to about 600 grams/liter, and suitable polar organic solvents include an alcohol, a polyol, a glycol ether, 1-methylpyrolidinone, pyridine, methylethylketone, or any combination thereof. Suitable non-polar organic solvents comprises tetrahydrofuran, toluene, xylene, a C-sub-5 ($C_5$) to C-sub-14 ($C_{14}$) branched paraffin, a C-sub-5 ($C_5$) to C-sub-14 ($C_{14}$) unbranched paraffin, N,N-dimethyl formamide, or any combination thereof.

The nanoparticles can be present in the range of from about 0.5 to about 70 wt %, the ligand can be present in the range of from about 0.5 to about 75 wt %, and the medium can be present in the range of from about 30 to about 98 wt %. The nanoparticles can be present in the range of from about 10 to about 60 wt %, the ligand can be present in the range of from about 1 to about 30 wt %, and the medium is present in the range of from about 30 to about 98 wt %. The nanoparticles can in other embodiments be present in the range of from about 15 to about 55 wt %, the ligand is present in the range of from about 2 to about 25 wt %, and the medium is present in the range of from about 30 to about 98 wt %. Also, the amount of ligand can be about 10% based on weight relative to the weight of the nanoparticles.

In one embodiment, the present invention involves the chemical reduction of metal salt in the presence of a ligand, which ligand is capable of complexing or bonding to the metal in a dispersing medium. The metal salt can be solvated by the solvent or dispersed in the solvent as a solid if the salt is insoluble in the solvent phase. Suitable solvents may include aqueous solvents substantially free of organic solvents. Suitable solvents can also include some polar organic solvents, e.g., if the metal salt can be solvated in a sufficiently high concentration, e.g., about 0.3 to about 0.9 M, or about 0.45 to about 0.7 M, or about 0.55 to about 0.6 M. The metal may include silver, copper, gold, zinc, cadmium, palladium, iridium, ruthenium, osmium, rhodium, platinum, iron, nickel, cobalt, indium, or any combination thereof. The salt anion may include nitrates, carboxylates, sulfates, or chlorides. The reducing agent must be of sufficient electrochemical potential and concentration to effectively reduce the respective metal salt. Strong reducing agents such as hydrazine, hydrazine hydrate, or hydrogen, that do not produce undesirable ionic byproducts are suitable; other reducing agents such as sodium borohydride may be used.

Ligands can be chosen on their ability to complex with metal particles and stabilize the particles against aggregation; one consideration is the ability of the ligand to allow the particles to consolidate and sinter during drying and thermal treatment. The temperature at which the particles sinter is in some part controlled by the ligand adsorbed to the metal. The ligand can be characterized as bonding to the metal through a heteroatom such as oxygen, sulfur, or nitrogen. In some embodiments the heteroatom portion of the ligand is provided as a carboxyl, sulfonyl, thiol, and the like. Without being bound to any particular theory of operation, it is believed that based on the relative thermal stability of the complexing portion and aliphatic backbone of the ligand compound, an intermediate salt may result during thermal treatment that adversely affecting the sintering of the metal nanoparticles. Ligands having a straight-chain aliphatic backbone comprising from about 1 to about 20 carbon atoms are particularly suitable. Branched or cyclic backbones having up to about 20 carbon atoms may be used, for example, if the ligand is sufficiently stable in the solvent system. Suitable ligands can preferably have from about 5 to about 12 carbon atoms in the aliphatic tail.

In the present invention, no post-synthesis treatment such as washing or phase transfer is needed in order to remove residual byproducts such as the metal salt anion. Although this step is not needed, additional washing and post-processing steps can be used. The byproducts of the reaction are left in the nanoparticle mixtures to catalyze the decomposition of the ligands on the nanoparticles surface. In particular, nitrate anions can react with organic acid ligands in self-propagating chemical decomposition or anionic oxidation-reduction synthesis of superconducting oxides to prevent intermediate metal salts. Alternatively, a compound such as an amine could be added to the reaction product or be part of the ligand molecule which similarly catalyzes the decomposition of the ligands and sintering of the nanoparticles. The particles are sometimes allowed to settle in order to concentrate them for forming films.

Without being bound by a particular theory of operation, it is believed that the metallic nanoparticles are able to remain dispersed in the aqueous phase by the formation of self-assembled surfactant structures, e.g., an interdigitated bi-layer, of the ligand or vesicle structures around the metallic nanoparticles. In other cases, the nanoparticles can phase separate from the aqueous phase giving rise to an oily ligand-rich phase comprising concentrated nanoparticles and a second aqueous phase. The particles can be stabilized by ligands binding to the surface of the silver through nucleophilic head groups with the aliphatic portion extending outward. The aliphatic portion of ligands not bound to the nanoparticle surface can associate with the aliphatic portion of the bound ligands forming a vesicle around the nanoparticle. Also without being bound to any particular theory of operation, it is believed that if no bi-layer formed, the metallic nanoparticles may phase-separate into an oily phase. Accordingly, ligands can form a bi-layer around the particles. The bi-layer can be broken down causing the nanoparticles to form a hydrophobic phase by either modifying the pH or by adding a salt or to the aqueous solution.

Accordingly, methods for synthesizing a metallic nanoparticle dispersion include reacting in an aqueous medium: at least one ligand, wherein the ligand comprises a heteroatom head group bonded to a tail comprising from 1 to about 20 carbon atoms; at least one reducing agent; and, at least one metallic salt in an aqueous dispersing solution, wherein the metallic salt is present in the dispersion at a concentration in the range of from about 10 grams/liter to about 600 grams/liter based on volume of the dispersing solution, and wherein the metallic salt comprises at least one cation comprising copper, gold, zinc, cadmium, palladium, iridium, ruthenium, osmium, rhodium, platinum, iron, nickel, cobalt, indium, or any combination thereof. Preferably the metallic salt comprises silver.

In many instances, the tail is as described elsewhere herein; suitable heteroatom head groups comprise oxygen, sulfur, nitrogen, and the like. A suitable ligand is characterized as being capable of binding by its heteroatom head group to a surface of a metallic nanoparticle so as to give rise to a metallic nanoparticle stabilized at least in part against aggregation.

Suitable reducing agents include strong reducing reagents that typically are capable of reducing metals in aqueous systems, e.g., hydrazine, hydrazine hydrate, hydrogen, sodium borohydride, lithium borohydride, ascorbic acid, a primary amine, a secondary amine, a secondary amine, a tertiary amine, and the like, or any combination thereof.

The metallic salt can include at least one anion, wherein the anion comprises acetate, nitrate, carboxylate, sulfate, chloride, hydroxide, or any combination thereof.

A suitable dispersing solution comprises an aqueous medium. Another suitable dispersing solution comprises an aqueous medium substantially free of organic solvents, and can comprise water. The dispersing solution can further comprise one or more polar organic solvents, one or more nonpolar organic solvents, or any combination thereof. Suitable polar and non-polar solvents are as described elsewhere herein.

Reacting can comprise contacting, mixing, stirring, sonicating, agitating, and the like; after reacting, one or more ligand heteroatom head groups are characterized as bound to a surface of one or more metallic nanoparticles so as to give rise to one or more metallic nanoparticles stabilized against irreversible aggregation.

The method can include combining the ligand and metallic salt in a respective molar ratio in the range of from about 0.1:1 to about 0.2:0.7, or even in the range of from about 0.1:1 to about 0.3:0.5; combining the metallic salt and reducing agent in a respective molar ratio in the range of from about 0.7:1 to about 1:2, in other cases the metallic salt and reducing agent in a respective molar ratio in the range of from about 4:1 to about 1:2, in other cases the metallic salt and reducing agent in a respective molar ratio in the range of from about 0.6:1 to about 1.2:1. The method can, in some embodiments, include adjusting the relative amounts of ligand, reducing agent, metallic salt, aqueous dispersing solution, adjusting the pH of the aqueous medium, or any combination thereof, so as to give rise to a pH in the range of from about 3 to about 12. In certain embodiments, the pH can vary between the basic and acidic regimes during the reaction.

In some configurations, the method can include heating the aqueous medium, ligand, reducing agent, and metallic salt in aqueous dispersing solution, or any combination thereof, to a temperature of from about 5 degrees Celsius to about 200 degrees Celsius prior to reaction; to a temperature of from about 35 degrees Celsius to about 70 degrees Celsius prior to reaction; or to a temperature of from about 40 degrees Celsius to about 60 degrees Celsius prior to reaction.

The method typically includes a recovery step following reaction. The recovery step can include allowing the passage of sufficient time such that the concentration of nanoparticles in any aqueous medium present after reaction can be in the range of from about 0 wt % to about 70 wt %, or in the range of from about 0.5 wt % to about 30 wt. %, or in the range of from about 2 wt % to about 20 wt. %, or in the range of from about 3 wt % to about 7 wt. %, and then recovering the reaction products. In some cases, the recovery step comprises allowing the passage of sufficient time such that the concentration of nanoparticles in any aqueous medium present can be in the range of from about 0.5 wt % to about 70 wt. %, or in the range of from about 5 wt % to about 60 wt. %, decanting the aqueous medium, recovering the reaction products, and ultrafiltration of the decanted aqueous medium to recover any nanoparticles residing in the decanted medium. In some cases, a cake comprising nanoparticles will be formed. Such a cake can have from about 25 wt. % to about 70 wt. %. In other embodiments, a supernatant is formed, which can comprise from 0 wt. % up to about 30 wt. % nanoparticles. Distribution of the nanoparticles can be distributed between supernatant and cake. The recovery step can include ultrafiltration of any aqueous medium present following reaction when there are no settled reaction products so as to recover nanoparticles present in the medium.

In some embodiments, the reacting comprises continuously introducing the aqueous medium, ligand, and reducing agent into a first stirred reactor capable of fluid communication with the contents of a second stirred reactor. Suitable medium, ligand, and reducing agent are described elsewhere herein, as are the suitable ratios of these entities to one another. The aqueous medium, ligand, reducing agent, and metallic salt in aqueous dispersing solution may be heated as set forth elsewhere herein. Typically, the residence time of the first reactor is sufficient to as to give rise to the reaction progressing to substantial completion, and the method can include continuously transporting the contents of the first reactor to the second reactor; the residence time in the second reactor is envisioned as sufficient to allow the reaction to progress to essentially total completion.

The methods described herein can also include one or more recovery steps.

Figure 1B:
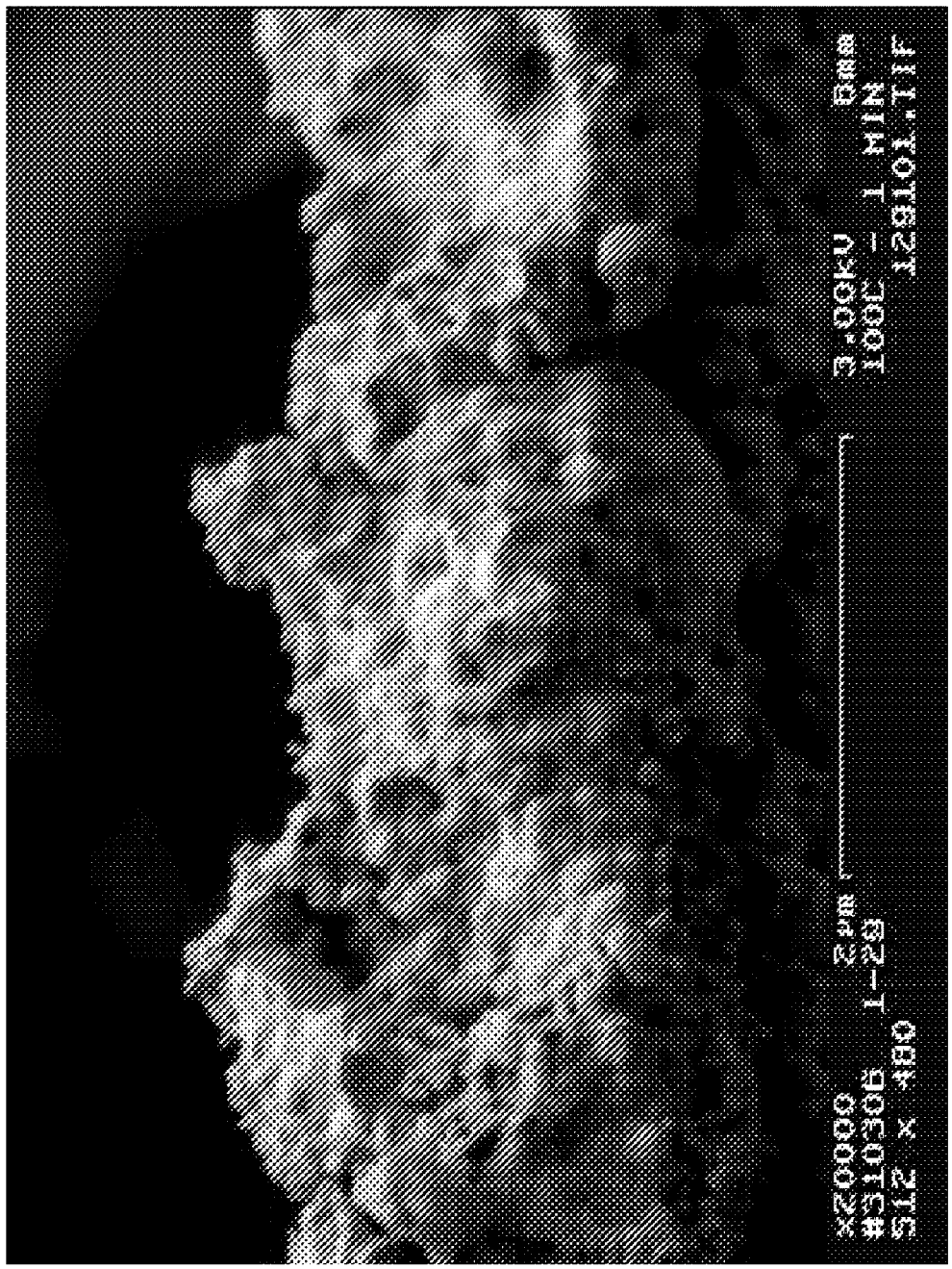
FIG. 1B illustrates an embodiment of a scanning electron microscope ("SEM") micrograph of a trace comprised of a composition of the present invention cured for 1 minute at 100 degrees Celsius.
Figure 1C:
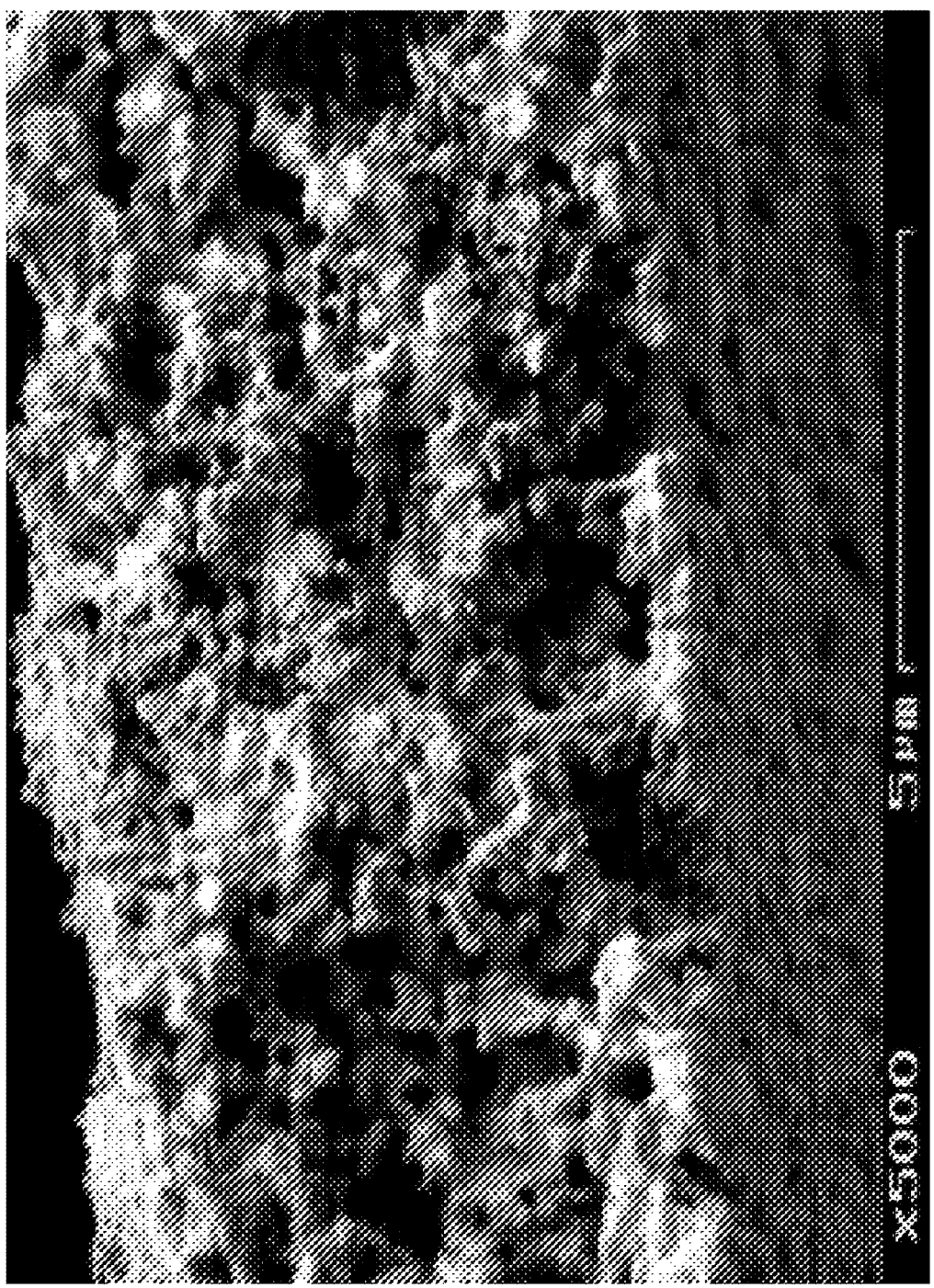
FIG. 1C depicts an embodiment of a SEM micrograph of a trace comprised of a composition of the present invention cured for 3 minutes at 85 degrees Celsius.

Metallic nanoparticles synthesized according to the present invention and the structures formed by curing these nanoparticles are shown in FIGS. 1(A), 1(B), and 1(C). FIG. 1(A) depicts silver nanoparticles made according to the present invention. As can be seen by comparison of the particles to the scale bar in FIG. 1(A), typical nanoparticles made in accordance with the present invention have widths of well under 100 nm. FIG. 1(B) depicts a structure formed by metallic nanoparticles made according to the present invention after curing at about 100 degrees Celsius for about 1 minute. FIG. 1(C) depicts a structure formed by metallic nanoparticles made according to the present invention after curing at about 85 degrees Celsius for about 3 minutes.

Figure 2:
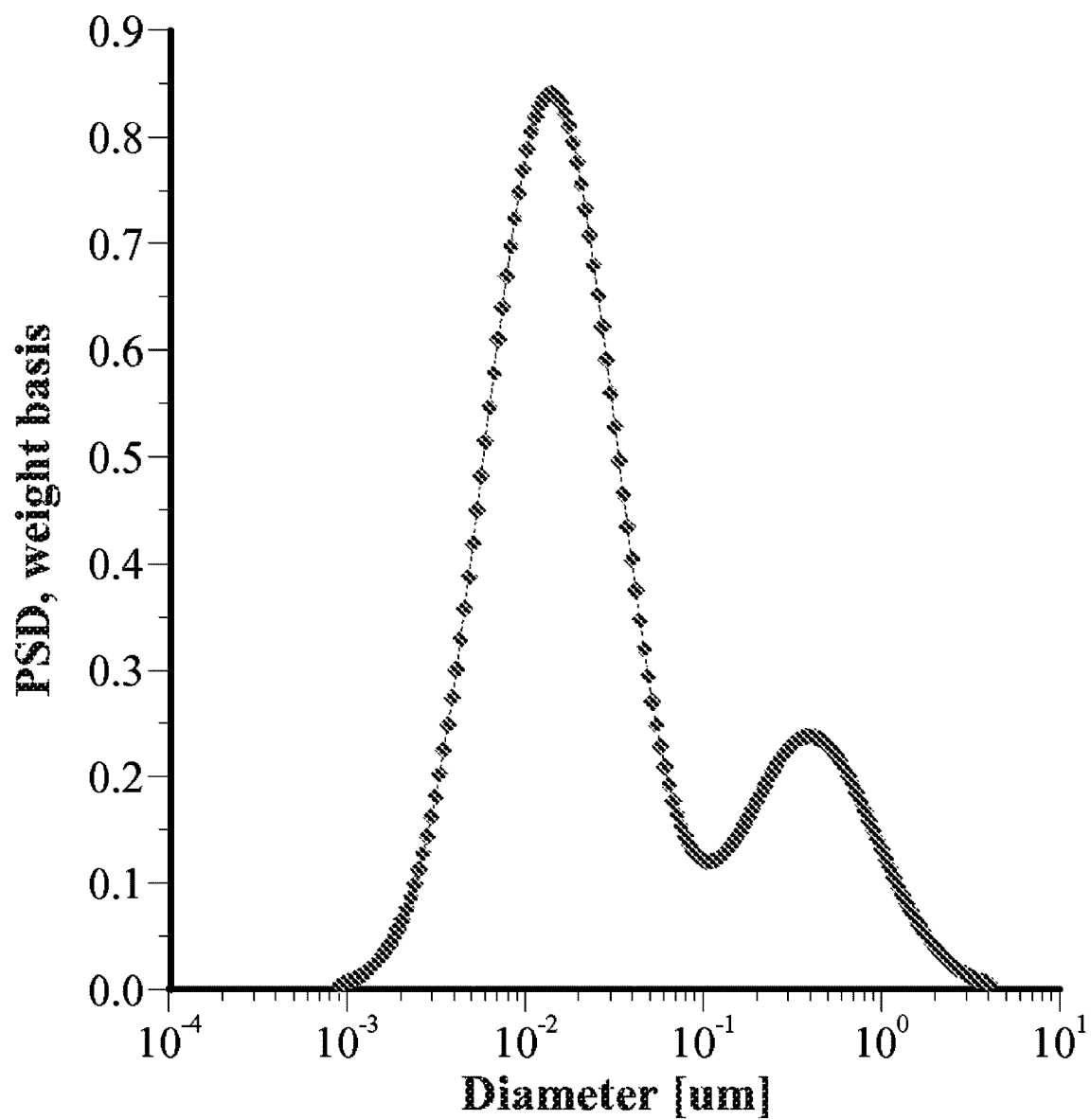
FIG. 2 depicts an embodiment of a particle size distribution, on a weight basis, of a composition of the present invention.

The existence of individual particles along with nanoparticle agglomerate in certain embodiments of the present invention is shown in FIG. 2. That figure depicts, on a weight basis, the proportion of individual metallic nanoparticles synthesized according to the present invention relative to nanoparticle agglomerate comprised of the individual nanoparticles.

Methods for forming a conductive structure on a substrate can include depositing a composition onto the substrate, wherein the composition comprises at least one population of metallic nanoparticles, at least a portion of the population comprising individual metallic nanoparticles characterized as having an average cross-sectional dimension in the range of from about 1 nm to about 30 nm; wherein each of the nanoparticles comprise at least one ligand bound to its surface, the ligand comprising a heteroatom head group bound to the nanoparticle surface and a tail bound to the heteroatom head group; and, curing the deposited composition.

The depositing can include a printing method; suitable printing methods can include flexographic printing, rotogravure printing, lithographic printing, intaglio printing, relief printing, screen printing, inkjet printing, laser printing, or any combination thereof.

As pertaining to the composition of these methods, typical populations of metallic nanoparticles are as described elsewhere herein, as are suitable ligands, and acceptable aqueous media.

A further consideration in formulating metallic nanoparticle-based inks is rheology. The ink rheology is influenced by the deformation behavior of the solid components and the flow behavior of the components. Mezger, T. G., The Rheology Handbook, 2002, published by Vincentz Verlag, Hannover, Germany; Verstrat, D. W., Research Report, Formulating with Associative Rheology Modifiers, Alco Chemical website, www.alcochemical.com., Alco Chemical Company, Division of National Starch and Chemical Company, Chattanooga, T N; Manshausen, P., Borchers GmbH, Monheim, Germany, Presented at the 6.sup.th Nurnberg Congress, April, 2001. These behaviors are responses to shear forces imparted on the ink during the process of depositing or printing the ink onto the desired substrate. Additives can modify the ink rheology such that the desired flow properties are achieved with minimal adverse affects on the electrical properties and adhesion of the metallic trace or film.

There are many choices for rheology modifiers, Manshausen, P., Borchers GmbH, Monheim, Germany, Presented at the 6.sup.th Nurnberg Congress, April, 2001; Young, V. L. and Hickman, A. D., Dow Latex Technotes, Jan. 6, 1992, including associative and non-associative organic thickeners, as well as inorganic thickeners. Associative thickeners generally associate with ingredients in the inks such as the metal nanoparticles and the polymeric binder particles incorporated for adhesion. Non-associative thickeners interact with the aqueous phase, essentially thickening the water.

The composition of the method can include one or more rheology modifiers. Some such modifiers can include an associative thickener such as hydrophobically modified polyether polyurethane, hydrophobically modified polyether, hydrophobically modified acrylic thickener, hydrophobically modified cellulose ether, and the like. Alternatively, the rheology modifier can include a thickening agent such as an alkali-soluble emulsion, such as a polymer comprising units polymerized from (meth)acrylic acid, wherein a suitable polymer comprises a homopolymer of (meth)acrylic acid, a co-polymer of (meth)acrylic acid and (meth)acrylate esters, maleic acid, or any combination thereof. A thickening agent can also include a cellulose based material such as hydroxyethyl cellulose, hydroxypropyl cellulose, arabinogalactin, dextran, starches, an acid swellable emulsion, a polyvinyl alcohol, a polyacrylamide, polyethylene glycol, or any combination thereof. Typically, a rheology modifier can be present in the range of from about 0 wt % to about 15 wt %, or in the range of from about 0 wt % to about 7 wt %, or even in the range of from about 0 wt % to about 3 wt %.

Preparation of a formulation that is viable as an ink to be printed on commercial printing equipment also typically requires the addition of agents to enable or enhance adhesion of the cured ink to the desired substrate, to enhance the wetting of the ink on the substrate, and to modify the rheological or flow characteristics of the ink.

In some embodiments, metallic nanoparticles will not adhere to untreated substrates that are commonly used such as polyester, polypropylene, and paper. Thus, adhesives, binders, or any combination thereof, may be added to the metallic nanoparticle dispersion such that additive establishes a chemical or physical bond with the surface of the desired substrate. Ideally, these additives do not prevent or hamper the process of curing or sintering the metallic nanoparticles into a continuous, conductive film or structure. In addition, the adhesion-enhancing additive should be chosen such that it does not affect the stability of the nanoparticles. Adhesion-promoting additives generally include surfactants that contribute to the ink wetting the substrate surface.

Accordingly, the composition of the disclosed method further comprises a binder, which can include a latex, any polymer soluble in the solvent medium of the nanoparticles, or compatible with the nanoparticles, a polymer latex, an emulsion polymer, polyimide, a silicone, a fluorocarbon, a polyamic acid, a polyurethane, a polyester, an epoxy, polyvinylalcohol, polyacrylamide, or any combination thereof. It is envisioned that the binder is present in the range of from about 0 wt % to about 20 wt %, or in the range of from about 0 wt % to about 7 wt %., or in the range of from about 0 wt % to about 5 wt %.

Substrates suitable for the method include a glass, a ceramic, a polymer, a silicon, a nitride, a carbides, a ceramic precursor, or any combination thereof. Suitable polymers include a polyester, a polyolefin, a polycarbonate, an acrylic polymer, polyethylene naphthalate, polyimide, polyamide-imide, polyvinyl chloride, polypropylene, a liquid crystal polymer, polycarbonate, or any combination thereof. In some embodiments, the substrate comprises paper, synthetic engineered paper, cardboard, a coated corrugated cardboard, uncoated corrugated cardboard, a fabric, and the like.

In some instances, it is envisioned that at least a portion of a surface of the substrate is capable of being modified to give rise to a surface capable of adhering to the deposited composition.

In some embodiments of the invention, the composition further comprises metallic particles. Such particles can have a width in the range of from about 200 nm to about 20000 nm, in the range of from about 500 nm to about 10000 nm, or in the range of from about 800 nm to about 3000 nm. Suitable particles comprise silver, copper, gold, zinc, cadmium, palladium, iridium, ruthenium, osmium, rhodium, platinum, iron, nickel, cobalt, indium, silver oxide, copper oxide, gold oxide, zinc oxide, cadmium oxide, palladium oxide, iridium oxide, ruthenium oxide, osmium oxide, rhodium oxide, platinum oxide, iron oxide, nickel oxide, cobalt oxide, indium oxide, or any combination thereof.

The curing aspect of the method typically comprises exposing the deposited composition to a temperature of less than about 110 degrees Celsius for less than about 90 seconds; a structure formed by the method typically has a thickness of less than about 20 micrometers; or exposing the deposited composition to a temperature of less than about 110 degrees Celsius for less than about 60 seconds; a structure formed by the method typically has a thickness of less than about 15 micrometers; or exposing the deposited composition to a temperature of less than about 140 degrees Celsius for less than about 30 seconds; a structure formed by the method typically has a thickness of less than about 15 micrometers; or exposing the deposited composition to a temperature of less than about 110 degrees Celsius for less than about 30 seconds; a structure formed by the method typically has a thickness of less than about 8 micrometers; or exposing the deposited composition to a temperature of less than about 140 degrees Celsius for less than about 20 seconds; a structure formed by the method typically has a thickness of less than about 8 micrometers.

Methods for forming a conductive structure include depositing a metallic nanoparticle composition onto the substrate, wherein the composition is capable of forming after curing at a temperature of less than about 110 degrees Celsius for less than about 90 seconds a cohesive and conductive structure having a resistivity in the range of from about 2 times to about 15 times the bulk resistivity of the corresponding metal and having a thickness of less than about 20 micrometers; and, curing the deposited composition.

Suitable deposition processes are described elsewhere herein. Nanoparticle compositions are envisioned as including a population of metallic nanoparticles, a ligand, a medium, or any combination thereof, all as discussed elsewhere herein.

Suitable compositions further can also include rheology modifiers as described elsewhere herein. The composition is envisioned as further comprising a binder, as described elsewhere herein. Suitable compositions may also include metallic particles, as detailed elsewhere.

Figure 3:
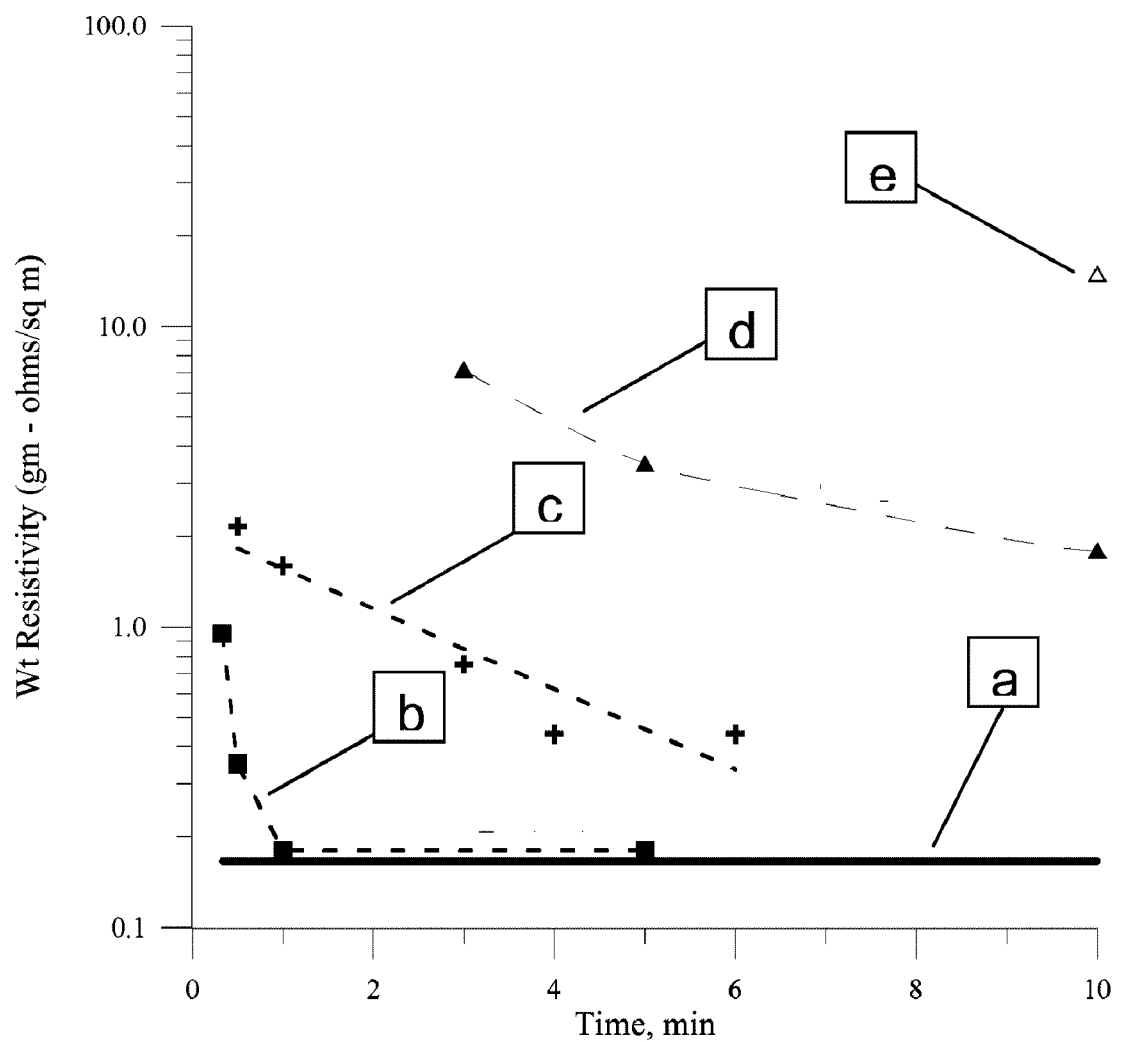
FIG. 3 depicts an embodiment of a graph showing the weight resistivity versus cure time for certain compositions provided by the present invention and for other compositions.
Figure 4:
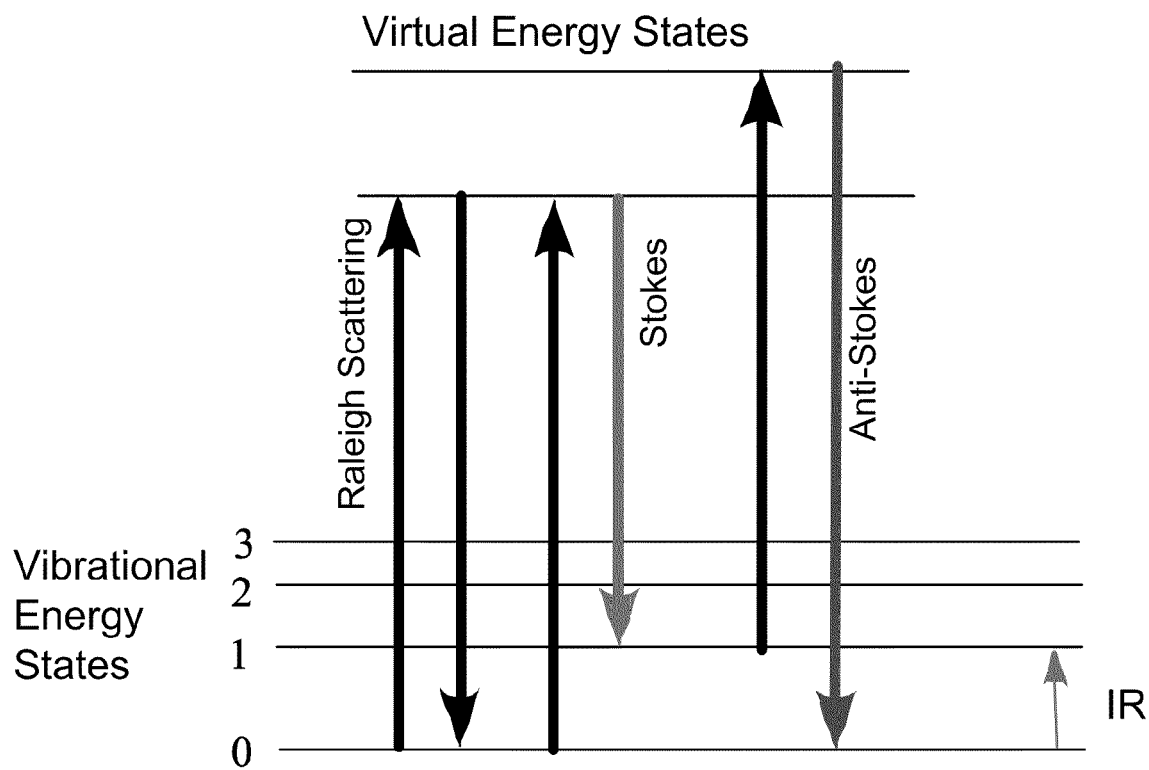
FIG. 4 depicts a graphic of an embodiment of a representation of the Raman spectrum

FIG. 3 depicts resistivity as a function of cure time for prior art compositions and compositions provided by the present invention. As shown, the resistivity of a composition comprising metallic silver nanoparticles synthesized by the present invention (trace (b)) achieve a resistivity comparable to that of bulk silver (trace (a)) after curing at a temperature of about 85 degrees Celsius for about 1 minute. Trace (c) represents a composition comprising metallic silver nanoparticles synthesized by the present invention and certain additives such as rheology modifiers and binders; as shown, that composition also approaches the resistivity of bulk silver after curing at a temperature of about 100 degrees Celsius for about 6 minutes. Trace (d) represents a composition produced by Sumitomo Metal Mining Co (Japan), http:www.smm.co.jp/b_info_E/b10_E.html, which composition, when cured at 150 degrees Celsius, achieved resistivity higher than that of compositions made according to the present invention at all cure times. Trace (e) represents a composition produced by Sumitomo (Japan), which, when cured at 100 degrees Celsius, and also is characterized as having a resistivity several orders of magnitude greater than that of compositions made according to the present invention at all cure times.

The following are non-limiting examples that are representative only and that do not necessarily restrict the scope of the present invention.

Example 1

An initial solution was prepared by adding 7.5 grams of ammonium hydroxide (30% ammonia by weight) to 275 grams of water; 13.5 grams of heptanoic acid was added to this solution followed by 20.9 grams of 50% hydrazine hydrate aqueous solution. The ammonium hydroxide is necessary to allow the acid to dissolve in the water. Separately, 36 grams of silver nitrate was dissolved in 175 grams of water. The silver nitrate solution was added to the initial solution while stirring under nitrogen. The resultant product was flocculated and allowed to settle. Excess water was decanted off. The concentrated product was spread onto 5 mil polyester film with a 0.5 mil wire wound rod and then cured at 80 degrees Celsius and 100 degrees Celsius for a time within a range of 1-2 minutes resulting in cohesive and conductive silver films.

Example 2

An initial solution was prepared by adding 2.1 grams of ammonium hydroxide (30% ammonia by weight) to 50 grams of water; 7.8 grams of heptanoic acid was added to this solution followed by 3 grams of 50% hydrazine hydrate aqueous solution. Separately, 10 grams of silver nitrate was dissolved in 50 grams of water. The silver nitrate solution was added to the initial solution while stirring under nitrogen. The resultant product was allowed to settle and the excess water decanted off.

The concentrated product was spread onto 5 mil polyester film with a 0.5 mil wire wound rod and then cured at 80 degrees Celsius and 100 degrees Celsius for a time period in a range of 1-2 minutes resulting in cohesive and conductive silver films. The weight resistivity of a sample cured at 100 degrees Celsius for 1 minute was measured to be 0.39 gram-ohms/meters squared (about 2 times bulk silver.)

Example 3

An ink composition was prepared by adding 50 grams of spherical silver powder (1-2 um mean diameter) to 50 grams of 35 wt % nanoparticle dispersion of the solution described in Example 1 also containing 3 wt % of an acrylic copolymer latex (55 wt % polymer), 2 wt % of polyvinyl alcohol (25 wt % in water, Mw of 8,000-9,000), and 1 wt % ethylene glycol. The materials were mixed together, and were milled using a mortar and pestle until a substantially homogeneous mixture was obtained. A film of the resulting ink was deposited onto 0.005 inch thick untreated polyester film with a 0.0015 inch Bird film applicator. The wet film was cured at 100 degrees Celsius for 30 seconds followed by 60 seconds at 140 degrees Celsius. The weight resistivity of the resulting silver films was measured to be 1.3 gram-ohms/meters squared, approximately 8 times the resistivity of bulk silver. The adhesion of the film to the substrate was tested by applying a 4" long strip of SCOTCH brand tape, manufactured by 3M Corporation, to the film. Good adhesion was ensured by applying pressure with the index finger (not the fingernail.) The tape was then rapidly removed, pulling upward at a 90 degree angle, perpendicular to the substrate. This tape test method is substantially similar to the ASTM D3359-02 Standard Test Method for Measuring Adhesion by Tape Test. Upon administering the above-described Tape Test, it was observed that there was slight removal of the silver from the bulk of the trace (4.215, with 5 being a clean tape), but substantially none of the silver was removed from the substrate. The slight removal was observed to be a cohesive failure between the silver particles.

Example 4

An ink composition was prepared by adding 50 grams of spherical silver powder (1-2 micron mean diameter) to 50 grams of 35 wt % nanoparticle dispersion also containing 10 wt % polyvinlacetate-polyethylene copolymer latex (50 wt % polymer), 2 wt % of polyvinyl alcohol (25 wt % in water, Mw of 8,000-9,000), and 1 wt % ethylene glycol. The materials were mixed together, and were milled using a mortar and pestle until a homogeneous mixture was obtained. A film of the resulting ink was deposited onto 0.005 inch thick untreated polyester film with a #16 wire wound rod (0.016 inch wire diameter, 0.001 inch wet film thickness). The wet film was cured at 100 degrees Celsius for 30 seconds followed by 30 seconds at 140 degrees Celsius. The weight resistivity of the resulting silver films was measured to be 1.0 gram-ohm/meters squared, approximately 6.2 times the resistivity of bulk silver. The adhesion of the film to the substrate was evaluated by utilizing the tape test method previously described in Example 3. The adhesion of the film to the substrate was very good (4.8/5), with only a trace of silver removed from the surface (cohesive failure), and substantially no silver removal from the substrate was observed.

Example 5

An ink composition was prepared by adding 25 grams of spherical silver powder (1-2 um mean diameter) to 50 grams of 35 wt % nanoparticle dispersion also containing 3 wt % acrylic copolymer (55 wt % polymer), and 4 wt % of polyacrylamide (50 wt % in water). The materials were mixed together, and were milled using a mortar and pestle until a homogeneous mixture was obtained. A film of the resulting ink was deposited onto 0.005 inch thick untreated polyester film with a #16 wire wound rod (0.016 inch wire diameter, 0.001 inch wet film thickness). The wet film was cured at 100 degrees Celsius for 30 seconds followed by 60 seconds at 130 degrees Celsius. The weight resistivity of the resulting silver films was measured to be 1.71 gram-ohms/meters squared, approximately 10.7 times the resistivity of bulk silver. The adhesion of the film to the substrate was evaluated by utilizing the tape test method previously described in Example 3. The adhesion of the film to the substrate was very good (4.8/5), with only a trace of silver removed from the surface (cohesive failure), and substantially no silver removal from the substrate was observed.

Example 6

An ink composition was prepared by adding 65 grams of spherical silver powder (1-2 pm mean diameter) to 80 grams of 35 wt % nanoparticle dispersion also containing 3 wt % acrylic copolymer (55 wt % polymer), 1.5 wt % of polyacrylamide (50 wt % in water), and 1 wt % propylene glycol. The materials were mixed together, and were milled using a mortar and pestle until a homogeneous mixture was obtained. A film of the resulting ink was deposited onto 0.005 inch thick untreated polyester film with a #16 wire wound rod (0.016 inch wire diameter, 0.001 inch wet film thickness.) The wet film was cured at 100 degrees Celsius for 30 seconds followed by 60 seconds at 130 degrees Celsius. The weight resistivity of the resulting silver films was measured to be 1.31 gram-ohms/meters squared, approximately 8 times the resistivity of bulk silver. The adhesion of the film to the substrate was evaluated using the Tape Test methods described in Example 3. The adhesion of the film to the substrate was good (4.215), with some removal (cohesive failure) of the silver from the bulk of the trace (4.215, with 5 being a clean tape), but substantially no silver removal from the substrate.

Example 7

An ink composition was prepared by adding 52 grams of spherical silver powder (1-2 micrometer mean diameter) to 64 grams of 35 wt % nanoparticle dispersion also containing 3 wt % acrylic copolymer (55 wt % polymer), 1.5 wt % of polyacrylamide (50 wt % in water), and 1 wt % propylene glycol. The materials were mixed together, and were further mixed in a vortex paint mixer for 5 minutes. A film of the resulting ink was deposited onto 0.005 inch thick untreated polyester film with a #16 wire wound rod (0.016" wire diameter, 0.001" wet film thickness). The wet film was cured at 60 degrees Celsius for 20 seconds followed by 40 seconds at 130 degrees Celsius. The weight resistivity of the resulting silver films was measured to be approximately 1.00 gram-ohms/meters squared, approximately 6 times the resistivity of bulk silver. The adhesion of the film to the substrate was evaluated by utilizing the tape test method previously described in Example 3. The adhesion of the film to the substrate was very good (4.9/5), with only a slight trace of silver removed from the surface (cohesive failure), and no silver removal from the substrate was observed. Additional samples were folded in expansive mode (single crease) and then compressive mode (single crease), and a hard crease was made with the tip of the finger (not the finger nail) on each sample. Minimal loss of conductivity was observed for each sample.

Example 8

An ink composition was prepared by adding 10 grams of Floetrol, manufactured by The Flood Company, to 40 grams of 35 wt % nanoparticle dispersion. The materials were mixed together and a film of the resulting ink was deposited onto 0.005 inch thick untreated polyester film with a 0.0005 inch diameter wire wound rod and then cured at 130 degrees Celsius for 90 seconds resulting in cohesive and conductive silver films. The adhesion of the film to the substrate was tested by applying a 4" long strip of SCOTCH brand tape, manufactured by 3M Corporation, to the film. Good adhesion was ensured by applying pressure with the index finger (not the fingernail.) The tape was then rapidly removed, pulling upward at a 90 degree angle, perpendicular to the substrate. This tape test method is substantially similar to the ASTM D3359-02 Standard Test Method for Measuring Adhesion by Tape Test. Upon administering the above-described Tape Test, it was observed that substantially no material was removed from the substrate.

Example 9

An ink composition was prepared by adding 10 grams of a 25 wt % solution of polyvinyl alcohol (9,000-10,000 Mw, 80% hydrolyzed) to 40 grams of 35 wt % silver nanoparticle dispersion. The materials were mixed together and a film of the resulting ink was deposited onto 0.005 inch thick polyester film with a 0.0005 inch diameter wire wound rod and then cured at 130 degrees Celsius for 90 seconds resulting in cohesive and conductive silver films. The adhesion of the film to the substrate was evaluated using the Tape Test method described above in Example 3. Upon carrying out the Tape Test, it was observed that some of the material was removed from the substrate, however, most of the ink remained on the substrate.

Example 10

A film of the as-prepared, 35 wt % silver nanoparticle dispersion was deposited onto 5 mil polyester film with a 0.0005 inch diameter wire wound rod and then cured at 85 degrees Celsius for 60 seconds resulting in cohesive and conductive silver films. The resulting film had a weight resistivity of 0.38 gram-ohms/m2 (IPC-TM-650, number 2.5.17.2). The adhesion of the film to the substrate was evaluated using the Tape Test method described above in Example 3. Upon carrying out the Tape Test, it was observed that substantially all of the material was removed from the substrate.

Example 11

An ink composition was prepared by adding 2.6 grams of a 1 or 2 wt % solution of commercially available hydrophobically modified hydroxyethylcellulose to 19.2 grams of 40 wt % silver nanoparticle dispersion. The materials were mixed together and a film of the resulting ink was deposited onto 0.005 inch thick polyester film with a 0.0003 inch diameter wire wound rod and then cured at 130 degrees Celsius for 90 seconds resulting in a cohesive and conductive silver film. The adhesion of the film to the substrate was evaluated using the Tape Test method described above in Example 3. Upon carrying out the Tape Test, it was observed that substantially all of the material was removed from the substrate.

Example 12

An ink composition was prepared by adding 0.5 grams of a solution of hydrophobically modified ethoxylated urethane rheology modifier to 10 grams of 34 wt % silver nanoparticle dispersion. The materials were mixed together and a film of the resulting ink was deposited onto 0.005 inch thick polyester film with a 0.0003 inch diameter wire wound rod and then cured at 100 degrees Celsius for 60 seconds resulting in a cohesive and conductive silver film. The adhesion of the film to the substrate was evaluated using the Tape Test method described above in Example 3. Upon carrying out the Tape Test, it was observed that substantially all of the material was removed from the substrate.

Example 13

An ink composition was prepared by adding 0.36 grams of Arabinogalactan wood gum (Larex Grade 100) to 18.2 grams of 35 wt % silver nanoparticle dispersion. The materials were mixed together and a film of the resulting ink was deposited onto 0.005 inch thick polyester film with a 0.0003 inch diameter wire wound rod and then cured at 100 degrees Celsius for 60 seconds resulting in a cohesive and conductive silver film. The adhesion of the film to the substrate was evaluated using the Tape Test method described above in Example 3. Upon carrying out the Tape Test, it was observed that some of the material was removed from the substrate.

Example 14

An ink composition was prepared by adding 0.63 grams of a 50 wt. % polyacrylamide solution (Aldrich 10,000 Mw) to 12.57 grams of 40 wt % silver nanoparticle dispersion. The materials were mixed together and a film of the resulting ink was deposited onto 0.005 inch thick polyester film with a 0.0003 inch diameter wire wound rod and then cured at 100 degrees Celsius for 60 seconds resulting in a cohesive and conductive silver film. The adhesion of the film to the substrate was evaluated using the Tape Test method described above in Example 3. Upon carrying out the Tape Test, it was observed that substantially none of the material was removed from the substrate.

Example 15

An ink composition was prepared by adding 0.44 grams of a 25 wt. % polyvinyl alcohol solution (Aldrich 9,000-10,000 Mw) and 1.14 grams of an acrylic nanoparticle latex dispersion to 22.2 grams of 35 wt % silver nanoparticle dispersion. The materials were mixed together and a film of the resulting ink was deposited onto 0.005 inch thick polyester film with a 0.0003 inch diameter wire wound rod and then cured at 130 degrees Celsius for 30 seconds resulting in a cohesive and conductive silver film. The adhesion of the film to the substrate was evaluated using the Tape Test method described above in Example 3. Upon carrying out the Tape Test, it was observed that some of the material was removed from the substrate.

Section B: Methods for Creating Analytical Substrates that can be Used in Surface Enhanced Raman Spectroscopy (SERS)

In some aspects, the ink composition described herein can be deposited onto a substrate to form an analytical substrate. In one embodiment, analytical substrates that can be used in Surface Enhanced Raman Spectroscopy (SERS) can be formed by depositing a metallic nanoparticle ink composition on a substrate and at least partially curing the ink composition. The resultant analytical substrate can be used to amplify a Raman signal to further analyze biological specimens or chemical compositions.

The analytical substrates described herein can be uniquely created, in one embodiment, by controlling the degree of cure of the nanoparticle inks after the inks are deposited onto the substrate. Partial curing of the ink can create a structure that can be used to amplify a Raman signal or a Raman scattering signal. Furthermore, partial curing of nanoparticle inks, especially for electronic applications is atypical because the resulting metal matrix likely does not have an optimum conductivity. Optimum conductivity typically is achieved when the ink is exposed to a predetermined temperature for a predetermined period of time. Each of the predetermined temperature and predetermined time period is typically a high enough temperature and a long enough time period to achieve the overall process of the cure that includes solvent removal and subsequent sintering of the metal nanoparticles. The methods described herein include interrupting the sintering process by curing the substrate for a shorter period of time. The metallic structures that result from the shorter cure cycles are structures that exhibit conductivity below a standard required for electronics applications. The resultant structure, however, may be ideal for amplifying the Raman signal by five or six orders of magnitude and is typically an inexpensive, reproducible product.

Figure 5:
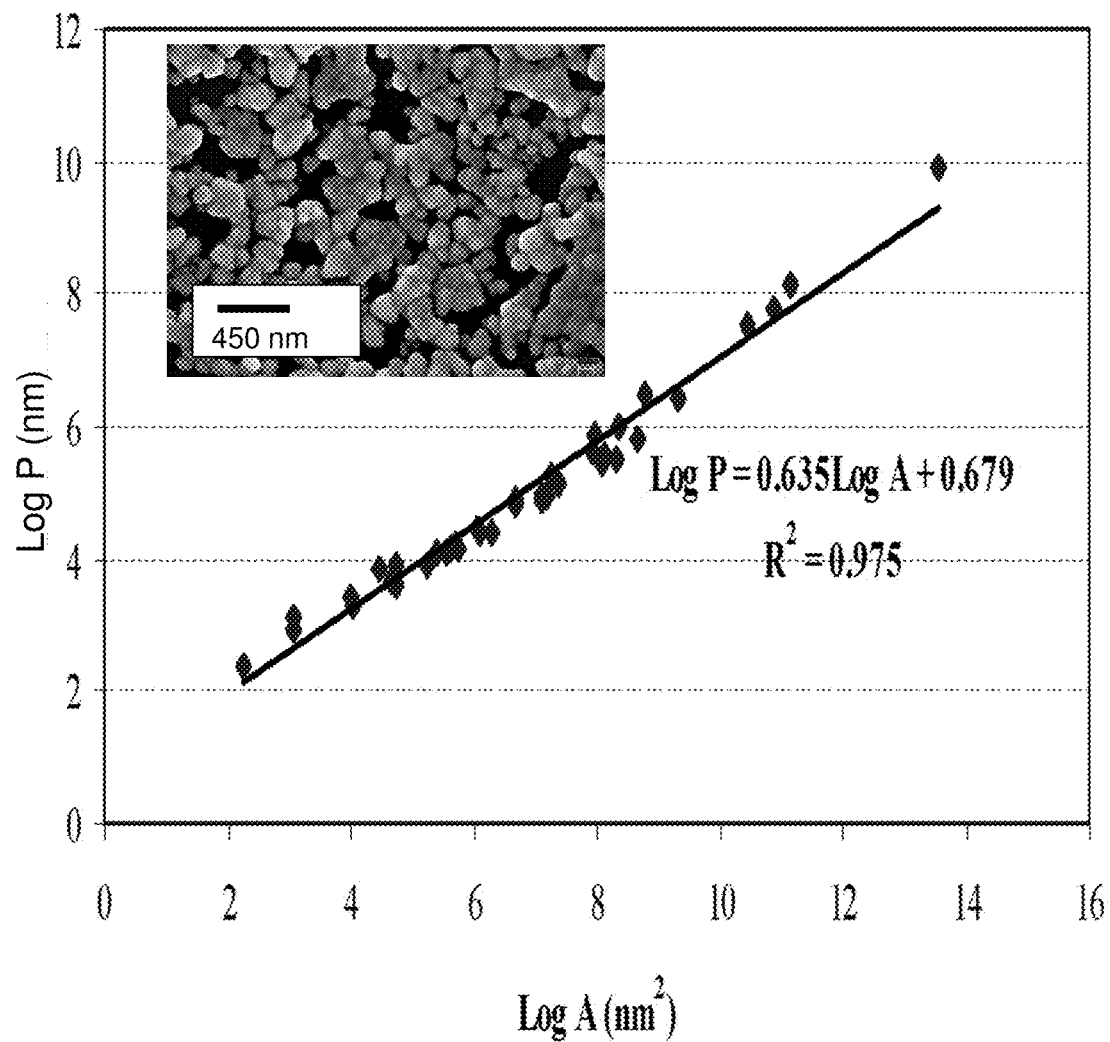
FIG. 5 depicts a graph of an embodiment of a SEM micrograph of the metal microstructure of a metallic nanoparticle structure created using the methods and systems described herein.

Illustrated in FIG. 5 is one embodiment of a SEM micrograph that depicts an embodiment of a colloidal film substrate consisting of metallic structures formed when metallic nanoparticle compositions are deposited on a substrate according to the methods described herein. As depicted in FIG. 5, the metallic nanoparticle structure can include one or more clusters of metallic nanoparticles connected to other clusters of metallic nanoparticle to form a web or network of metallic nanoparticles or metallic nanoparticle clusters. Also illustrated in FIG. 5 is a log-log graph of the cluster areas and perimeters of the microstructure from which a metallic nanoparticle signal amplifier can be obtained.

Unlike typical SERS substrate fabrication methods described herein, the analytical substrates described herein can be fabricated to form small clusters of metallic nanoparticles connected by weak links. The size or bulk of the links or connections between the metallic nanoparticles or metallic nanoparticle clusters can, in some embodiments, be controlled using the cure processes described herein. In one embodiment, the web or network of metallic nanoparticles can be created by controlling the thermal treatment of the metallic nanoparticles once they are deposited on a substrate. Controlling the thermal treatment of the metallic nanoparticles can include controlling a cure temperature or a cure time. In some embodiments, the cure process is controlled so that the metallic nanoparticles are partially sintered.

Using the methods described herein, metallic nanoparticle structures can be formed on a substrate surface to create an analytical substrate that will enable SERS amplification. The dimers, trimers and other clusters created when the metallic nanoparticles are deposited and at least partially cured, can form metallic nanostructures that include metallic colloidal particles which can further provide hyper-enhancement for various linear and nonlinear optical responses, including those associated with Raman spectroscopy. This enhancement, created by the metallic nanostructure parts, can result from the localization of optical plasmon excitations within small sections ("hot-spots") of a metallic nanostructure or cluster of partially cured metallic nanoparticles. These "hot spots," can be much smaller (on the order of tens of nanometers) than the size of the metallic nanoparticle structures formed on the substrate and can be much smaller than the wavelength of light used by the spectrometer. A hot spot, in one embodiment, can be a junction or cavity formed between two or more nanoparticles within the metallic nanoparticle structure formed on the substrate as a result of the methods and processes described herein. In one embodiment, the modification of the cure process can alter the interparticle spacing between the nanoparticles within the metallic nanoparticle structure thereby forming hot spots, junctions or cavities. The SERS effect, in some embodiments, can take place because of the creation of the hot spots. In particular, the cure process can be modified to include a predetermined cure temperature less than approximately 100 degrees Celsius and a predetermined cure time less than 30 seconds. The result of this cure process, in some embodiments, is a metallic nanoparticle structure that has an optimum interparticle spacing that optimally amplifies a Raman signal.

The metallic nanoparticle structures can be scale-invariant, unlike translationally invariant media, and therefore typically can not support propagating waves and so can not 'trap' electromagnetic field in very small volumes. When sufficiently concentrated, the large electromagnetic fields in the hot spots can result in very large SERS enhancement. The small areas, where the optical plasmon excitations are localized, may have very different local structures and, therefore, are characterized by different resonant frequencies. The various nano-scale areas, where the resonant plasmon excitations are localized, can act as a collection of different optical "nano-resonators," which can result in a distribution of resonance frequencies in the visible and IR spectral ranges and can have resonance quality-factors as large as $10^3$. When Stokes shifts are small, the SERS signal is roughly proportional to the local field raised to the fourth power and, therefore, it can be enhanced up to $10^{12}$ in the hot spots present within the metallic nanostructure.

In some embodiments, the resulting analytical substrate can magnify Raman signals by a factor of 10,000. In other embodiments, the resulting analytical substrate can magnify Raman signals by a factor in the range of 10,000 to 1,000,000. The magnification factor is in some embodiments a signal intensity factor. In other embodiments, the magnification factor can be a signal intensity factor at a particular wavelength of incident light.

Figure 6:
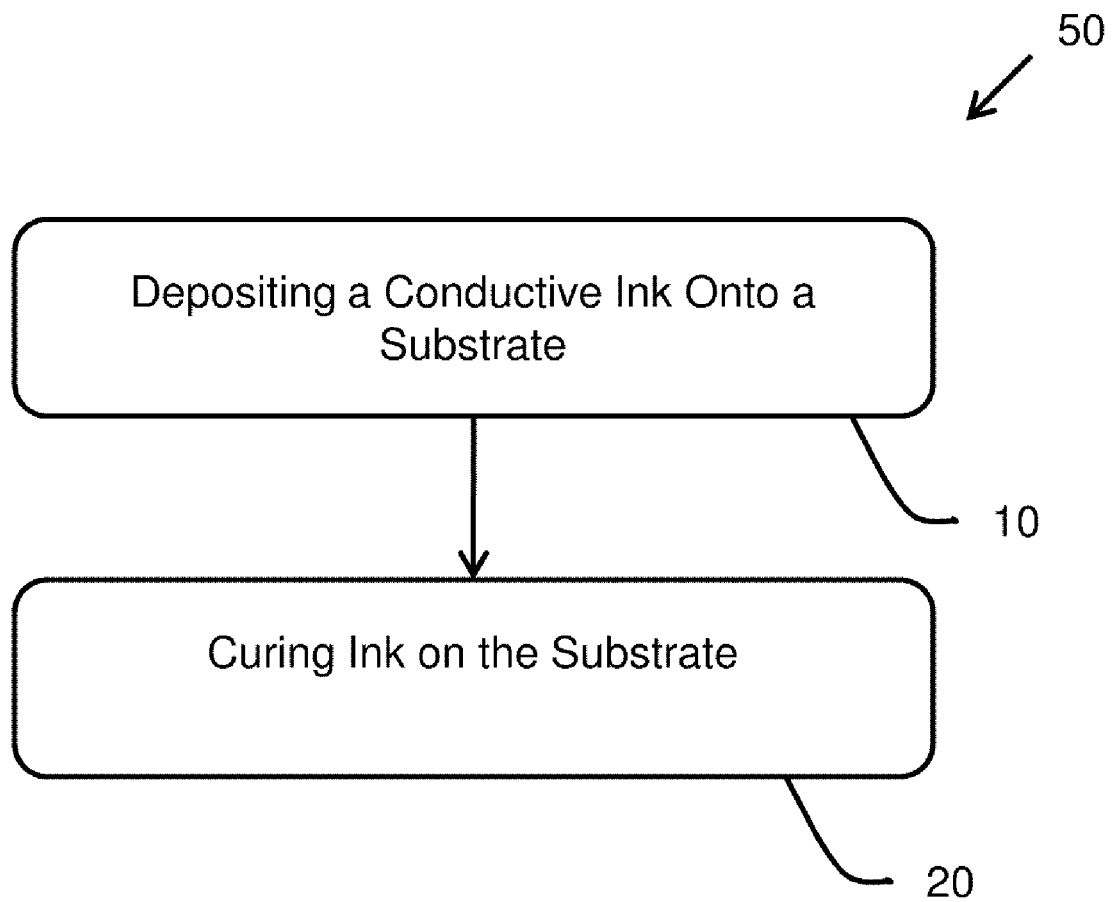
FIG. 6 depicts a block diagram illustrative of an embodiment of a method for applying a metallic nanoparticle-based ink to a substrate.

In some embodiments, the analytical substrates described herein can be fabricated or otherwise manufactured in accordance with the process illustrated in FIG. 6. FIG. 6 illustrates an embodiment of a method 50 for creating the substrates described herein, where the method includes depositing a conductive ink onto a substrate (Step 10) and curing the ink on the substrate (Step 20). In some embodiments, curing the ink can include curing the ink to a stable state which can support the deposition of a sample, dry or liquid, without being removed.

Further referring to FIG. 6, and in more detail, while the method 50 describes depositing a conductive ink onto a substrate, in other embodiments the method 50 can include depositing a metallic nanoparticle dispersion, a population of metallic nanoparticles, or any other composition that includes one or more metallic nanoparticles. In some embodiments, the ink composition can be any ink composition, metallic nanoparticle composition, conductive ink, or metallic nanoparticle dispersion described herein. In one embodiment, the ink composition can include one or more metallic nanoparticles. In some embodiments, these metallic nanoparticles can be any metallic nanoparticle described herein.

In one exemplary embodiment, the ink composition can be a metallic nanoparticle dispersion described herein. The dispersion can include one or more metallic nanoparticles where the metallic nanoparticles can have a width in a range of 1 nanometer to 100 nanometers. In still other embodiments, the dispersion can include one or more metallic nanoparticles that include at least one ligand bound to a surface of the nanoparticle, where the ligand can include a heteroatom group bound to the nanoparticle surface and a tail bound to the heteroatom group. In still another embodiment, the dispersion can include a particle agglomerate that includes two or more individual metallic nanoparticles, a nanoparticle floc that includes two or more individual metallic nanoparticles, or any combination of a particle agglomerate or a nanoparticle floc.

In one embodiment, the conductive ink deposited on the substrate is a metallic nanoparticle-based ink such as the ink manufactured by PCHEM ASSOCIATES of Bensalem, Pa. Some embodiments utilize a metallic ink comprised of metallic nanoparticles dispersed in an aqueous medium, where the metal can be any of silver, palladium, or any other conductive metal or metal oxide able to be deposited via the methods and systems described herein. Still other embodiments contemplate the deposition of a metallic conductive ink able to be deposited onto a substrate via the methods and systems described herein.

In some embodiments, the ink composition can be deposited onto the substrate using any deposition method described herein. In particular, the ink composition can be deposited onto the substrate using any of the printing techniques described herein, by spraying or spreading the ink composition onto the substrate, by dipping the substrate in the ink composition, or by depositing the ink composition onto the substrate using any of the application or deposition methods described herein. While in one embodiment, the ink composition can be deposited on substantially the entire surface of the substrate, in other embodiments the ink composition can be deposited on a portion of the surface of the substrate. In still other embodiments, the ink composition can be deposited in a pattern on the substrate.

Still other deposition techniques include: printing; spray coating; curtain coating; dip coating; roller coating; and any other method or process of liquid or powder deposition able to deposit a conductive ink onto a substrate. Embodiments where the conductive ink is deposited via printing the ink onto the substrate, the printing can be accomplished via any one of the following print methods: flexography; screen printing; gravure printing; ink jet printing; and any other printing method or technique able to deposit a conductive ink onto a substrate. Some embodiments include a method of depositing the ink onto the substrate such that the substrate can function as a Faraday cage. In these embodiments, the ink can be deposited such that it forms any one of the following patterns: a continuous film; a wire mesh pattern; a series of dots or marks; a series of lines; or randomly placed markings.

In one exemplary embodiment, a large area SERS substrate can be inexpensively achieved by printing arrays or patterns of lines or dots of the nanoparticle inks on larger substrates. The substrate, in this embodiment, can be a substrate larger than 1 centimeter square. By printing an array or lines, dots, markings, patterns, or other geometric shapes on a larger area substrate, it is possible to produce substrates that can be many meters long and more than one meter wide. Large area SERS substrates can increase the collection efficiency by several orders of magnitude. When detecting trace amounts of toxins or biochemicals dispersed in large volumes, the collection efficiency of the Raman spectrometer is directly proportional to the area of the SERS substrate. Thus, the larger the area of the SERS substrate, the greater the collection efficiency.

In one embodiment, a process for preparing SERS substrates can include printing lines 0 mm to 1 mm wide and less than 1 micrometer thick of the metallic nanoparticles described herein on a substrate. The metallic nanoparticles, once deposited, are then at least partially cured which results in the partial sintering of the nanoparticles. By varying the curing time, different levels of sintering can be achieved and different levels of Raman signal enhancement can be realized. In one embodiment, by varying the curing time and/or the curing temperature, different levels of sintering can be achieved and therefore different nanoparticle networks can be created. For example, partial sintering of the nanoparticles can produce a network of nanoparticles where the links between nanoparticles and nanoparticle clusters are weak. In this embodiment, the weak links contribute to the creation of hot spots. In another embodiment, the process can include depositing or printing an array of dots of the metallic nanoparticles on a substrate. The resulting array of dots can be used as deposit points for a sample which can then be analyzed using Raman spectroscopy. In one embodiment, the metallic nanoparticles can be deposited in any one of an array of lines, dots, markings, patterns, geometric shapes, or other marking(s) covering an area of the substrate such that when applied to the substrate, the substrate can act as an amplifier when used in a Raman spectrometer.

In some embodiments, the substrate can be any substrate capable of accepting the ink composition or capable of withstanding the heating process. In some embodiments, the substrate can be made of any of the following materials: glass; quartz; polyester; polyethylene; liquid crystal polymer (LCP); polypropylene, polymide; paper; an engineered polymer (PET, PEN, PVC, polycarbonate, polyamide, et. al.); a paper based material (coated, uncoated, board stock, corrugated, engineered paper, et. al.); a ceramic material; a silicon based material; or any other substrate compatible with the partial curing process and metallic nanoparticle dispersions described herein. In one embodiment, the substrate can be any substrate described herein. In some embodiments, the substrate can first be coated with one or more adhesion promoting layer prior to depositing the ink composition onto the substrate. In another embodiment, the ink composition can be deposited directly onto the substrate.

Curing the ink on the substrate can include heating the substrate to a predetermined temperature for a predetermined period of time. The substrate, in some embodiments, can be cured at a temperature less than 140 degrees Celsius for a period of time less than 60 seconds. In other embodiments, the substrate can be cured at a temperature in a range of 30 degrees Celsius to 100 degrees Celsius. In still other embodiments, the substrate can be cured for a period of time in a range of 5 seconds to 30 seconds.

Example 1

Figure 7:
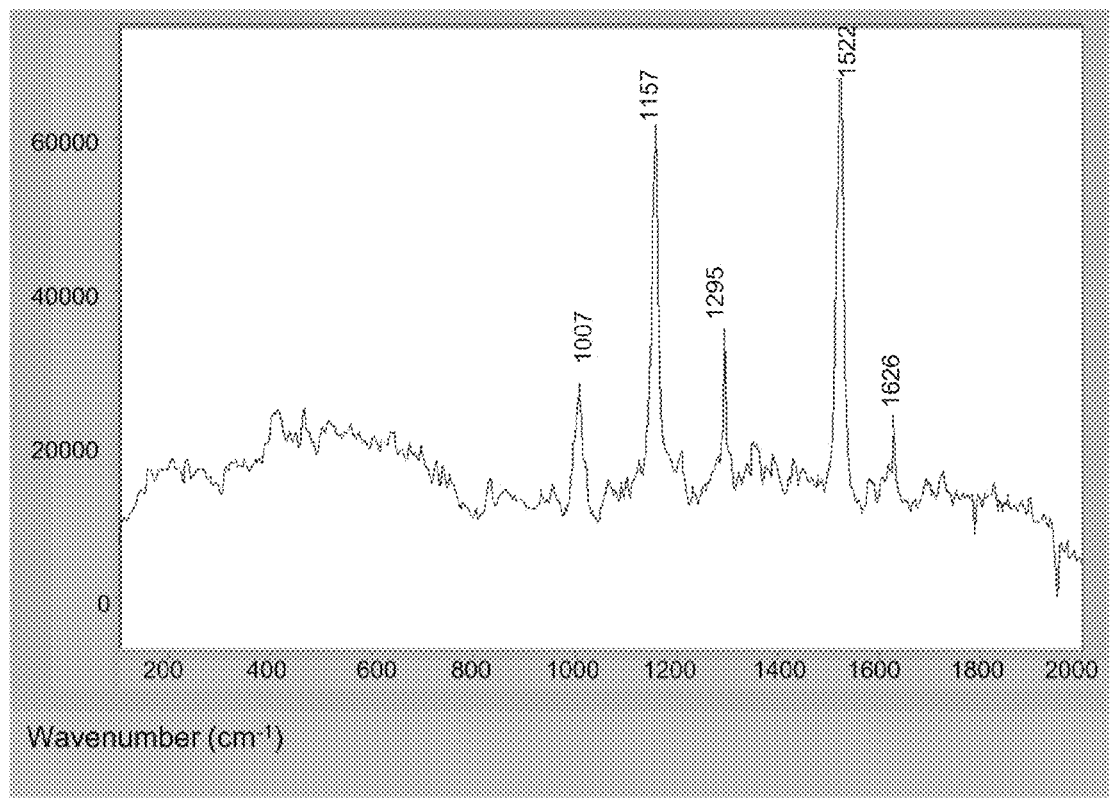
FIG. 7 depicts a graph of an embodiment of a spectrum created by scanning a carrot with a Raman Spectrometer using the substrates described herein.

In one instance, a silver nanoparticle based conductive ink formulation, such as the ink compositions and metallic nanoparticle dispersions described herein, was flexographically printed onto a 3 mil thick polyester film substrate. The screen pattern printed, e.g. lines having a width in a range of 30-60 micrometers and spaces having a width in a range of 200-300 micrometers, effectively forms a series of sites that can amplify a Raman signal. Measuring the resistance of the deposited lines showed the sheet resistance to be 5-10 ohms/sq. A simple demonstration of the effectiveness of this substrate involves the identification of β-carotene. This is accomplished by gently touching the above prepared SERS film substrate with a piece of freshly chopped carrot with no other sample preparation. The sample was then scanned by a Raman Spectrometer and the resulting spectrum is illustrated in FIG. 7.

Example 2

Figure 8:
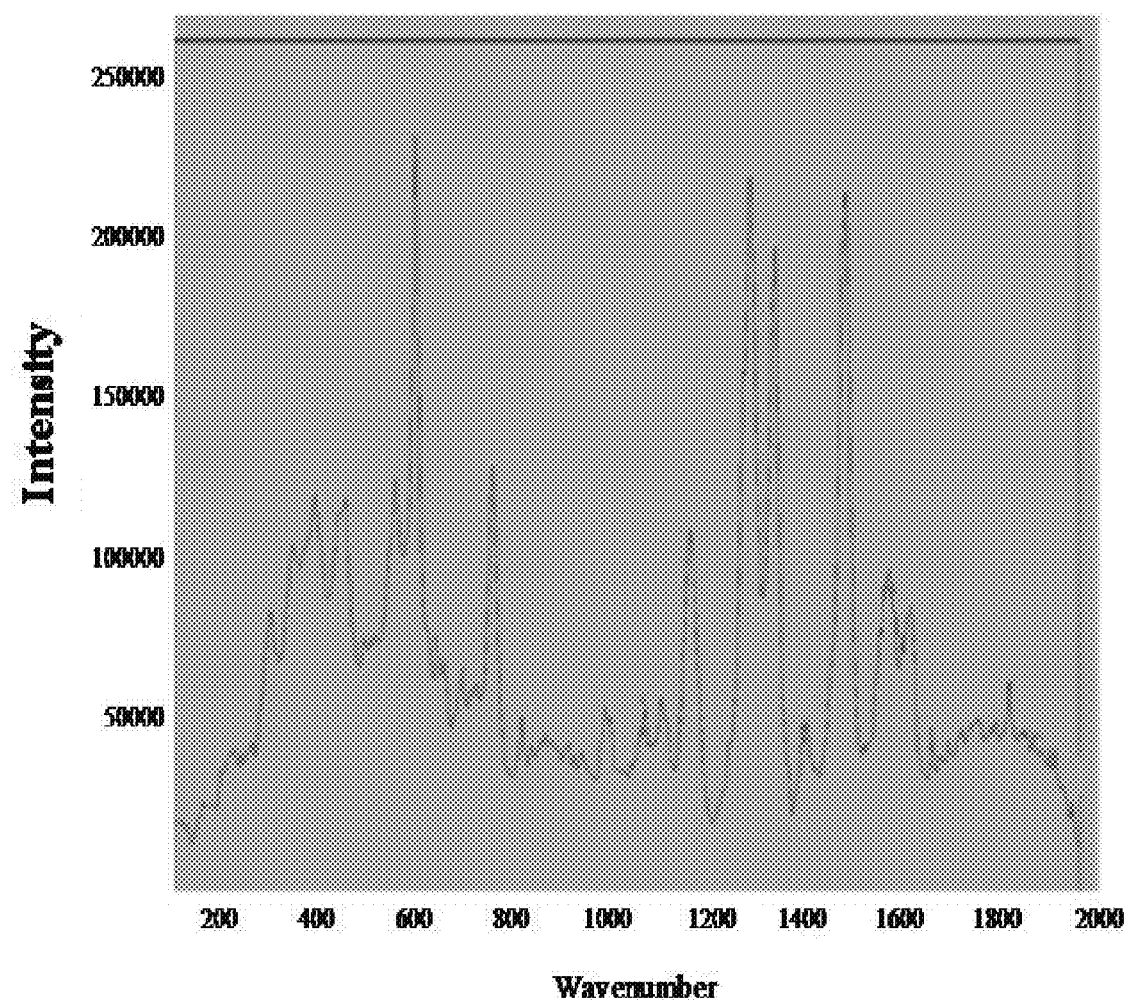
FIG. 8 depicts a graph of an embodiment of a spectrum created by scanning Rhodamine-6G, as found in distilled water, with a Raman Spectrometer using the substrates described herein.

The next example resulted in the SERS spectrum for Rhodamine-6G in distilled water depicted in FIG. 8. The substrate was prepared by depositing a metallic nanoparticle-based ink, such as the ink compositions and metallic nanoparticle dispersions described herein, onto a glass slide and at least partially curing the deposited ink at room temperature (e.g. 20-30 degrees Celsius) for 24 hours. Under these conditions, minimal sintering of the metallic nanoparticles may occur. The thickness of the cured nanoparticles was measured to be 1-2 microns. The very low concentration of the sample (two microliters of 5.0 nanomolar solution) and the subsequent strong signal obtained in the spectrum illustrates the advantageous signal amplification provided by the at least partially cured nanoparticles.

Example 3

Figure 9:
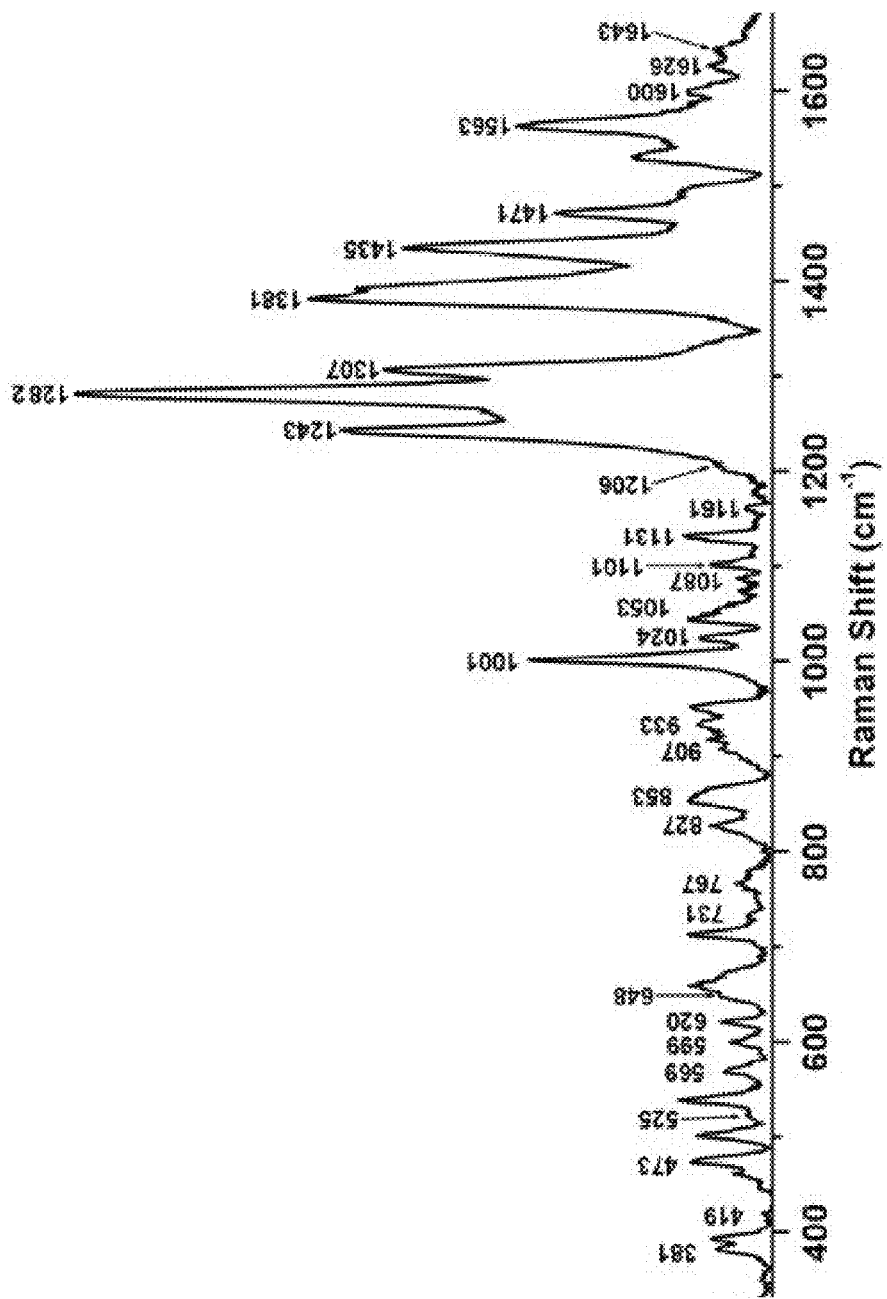
FIG. 9 depicts a graph of an embodiment of a spectrum created by scanning a lysate of a genetically modified 293 human epithelial kidney cell line (Phoenix-eco cells #102), with a Raman Spectrometer using the substrates described herein.

FIG. 9 depicts a spectrum resulting from the analysis of a biological sample, Lysate of a genetically modified 293 human epithelial kidney cell line (Phoenix-eco cells #102,) which was deposited onto a SERS substrate. The SERS substrate was fabricated using the methods described herein and using the metallic nanoparticle dispersions described herein. The resulting spectrum illustrated in FIG. 6 depicts the spectrum after fluorescence background subtraction. All lines in the spectrum can be identified using known analysis methods.

Example 4

In one example, a metallic nanoparticle ink composition was prepared by adding the following to 50 grams of 45 wt % aqueous silver nanoparticle dispersion, such as the nanoparticle dispersions described herein, 3 wt % Latex LO43 1 (55 wt % polymer), 2 wt % of polyvinyl alcohol (25 wt % in water, $M_w$ of 8,000-9,000), and 1 wt % ethylene glycol. The materials were mixed together until a homogeneous mixture was obtained. A film of the resulting ink was deposited onto a 0.005 inch thick print treated polyester film with a #4 Meier rod. The wet film was cured in a 100 degrees Celsius oven for 30 seconds. The sheet resistance of the resulting silver film was measured to be 300 milliohms/sq at the cured thickness which was not measured. The film was observed to have a dull gold coloring. The adhesion of the film to the substrate was tested by applying a 4" long strip of SCOTCH brand tape, manufactured by the 3M Corporation, to the film. Once adequate adhesion of the tape to the film was insured by applying pressure with the index finger (not the fingernail), the tape was then rapidly removed by pulling upward at a 90 degree angle perpendicular to the substrate. This tape test method is substantially similar to the ASTM D3359-02 Standard Test Method for Measuring Adhesion by Tape Test. Upon administering the above-described Tape Test, it was observed that there was no removal of the silver from the bulk of the trace (e.g. the deposited and at least partially cured ink on the substrate.)

Using the above-generated analytical substrate, a sample was prepared by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 100,000 counts.

Example 5

Using substantially the same ink composition of Example 4, a film of the ink was deposited onto 0.005 inch thick print treated polyester film with a #4 Meier rod. The wet film was cured in a 100 degrees Celsius oven for 5 seconds. The sheet resistance of the resulting silver film was measured to be 2 ohms/sq at the cured thickness which was not measured. The film was observed to have a slightly gray coloring. The adhesion of the film to the substrate was tested by applying a 4 inch long strip of SCOTCH brand tape, manufactured by the 3M Corporation, to the film. Good adhesion was ensured by applying pressure with the index finger (not the fingernail.) The tape was then rapidly removed, pulling upward at a 90 degree angle, perpendicular to the substrate. This tape test method is substantially similar to the ASTM D3359-02 Standard Test Method for Measuring Adhesion by Tape Test. Upon administering the above-described Tape Test, it was observed that a slight amount of silver was removed from the bulk of the trace (e.g. the deposited and at least partially cured ink on the substrate.)

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 220,000 counts.

Example 6

Using substantially the same ink composition prepared in Example 4, a film of the ink was deposited onto a 0.005 inch thick print treated polyester film with a #4 Meier rod. The wet film was cured in a 140 degrees Celsius oven for 10 seconds. The sheet resistance of the resulting silver film was measured to be 50 milliohms/sq at the cured thickness which was not measured. The film was observed to be have a dull gold coloring. The adhesion of the film to the substrate was tested by applying a 4 inch long strip of SCOTCH brand tape, manufactured by the 3M Corporation, to the film. Good adhesion was ensured by applying pressure with the index finger (not the fingernail.) The tape was then rapidly removed, pulling upward at a 90 degree angle, perpendicular to the substrate. This tape test method is substantially similar to the ASTM D3359-02 Standard Test Method for Measuring Adhesion by Tape Test. Upon administering the above-described Tape Test, it was observed that substantially no silver was removed from the bulk of the trace (e.g. the deposited and at least partially cured ink on the substrate.)

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 60,000 counts.

Example 7

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto 0.003 inch thick print treated polyester film (Melinex 454). The wet film was cured in a 80 degrees Celsius oven for 15 seconds. The sheet resistance of the resulting silver film was measured to be 10 ohms/square at the cured thickness which was not measured. The silver printed squares were observed to be gray colored.

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 240,000 counts.

Example 8

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto a 0.010 inch thick paper (NewPage 40# Propoint). The wet film was cured in a 80 degrees Celsius oven for 15 seconds. The resulting silver film was not conductive. The silver printed squares were observed to be gray colored.

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 40,000 counts.

Example 9

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto a 0.010 inch thick paper (NewPage 40# Propoint). The wet film was cured in a 100 degrees Celsius oven for 30 seconds. The sheet resistance of the resulting silver film was measured to be 0.8 ohms/square at the cured thickness which was not measured. The silver printed squares were observed to be dull gold colored.

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 180,000 counts.

Example 10

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto a 0.003 inch thick print treated polyester film (Melinex 454.) The wet film was cured in a 100 degrees Celsius oven for 5 seconds. The sheet resistance of the resulting silver film was measured to be 2 ohms/square at the cured thickness which was not measured. The film was observed to be slightly gray colored. The sample was stored in an unsealed plastic bag for 30 days under ambient conditions.

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 80,000 counts.

Example 11

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto a 0.003 inch thick print treated polyester film (Melinex 454.) The wet film was dried in a 80 degrees Celsius oven for 5 seconds. The resulting silver film was not conductive. The film was observed to have a gray coloring.

A sample was prepared using the above substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 30,000 counts.

Example 12

Using substantially the same ink composition prepared in Example 4, one centimeter square analytical substrates were printed using a lab scale flexographic printer. These substrates included depositing the ink composition onto a one centimeter square area of the substrate. An eight (8) BCM Anilox roll was used to deposit a film of the ink composition onto the print plate and subsequently onto 0.003 inch thick print treated polyester film (Melinex 454.) The wet film was dried in a 80 degrees Celsius oven for 5 seconds. The resulting silver film was not conductive. The film was observed to have a gray coloring. The sample was stored in a sealed plastic bag for 30 days under ambient conditions.

After 30 days, the sheet resistance of the resulting silver film was measured to be 20 ohms/square at the cured thickness which was not measured. A sample was prepared using this substrate by depositing a single drop of 10 nanomolar solution of Rhodamine-6G in distilled water onto the silver on the PET film. The resulting sample was immediately analyzed using a 785 Near Infrared Raman spectrometer at an excitation wavelength of 785 nanometers. The signal produced was that of Rhodamine-6G and the signal strength of the double set of peaks at a wavenumber of approximately 1280 l/cm was 190,000 counts.

The above-mentioned methods and compositions are not to be limited to any devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination. Further, reference to values stated in ranges include each and every value within that range.

What is claimed is:

1. A method for fabricating a substrate that amplifies Raman signals, the method comprising:
    depositing, on a substrate, a film comprising a metallic nanoparticle dispersion that comprises a metallic nanoparticle population; and
    heating the substrate to a temperature less than 100 degrees Celsius for a period of time less than 30 seconds to generate a substrate for amplifying a Raman signal by a factor greater than 10,000.

2. The method of claim 1, wherein depositing the film further comprises depositing the film comprising metallic nanoparticles having an average cross-sectional dimension in a range of about 1 nm to about 100 nm.

3. The method of claim 1, wherein depositing the film further comprises depositing the film comprising metallic nanoparticles wherein each nanoparticle comprises at least one ligand bound to a surface of the nanoparticle, the ligand comprising a heteroatom head group bound to the nanoparticle surface and a tail bound to the heteroatom head group.

4. The method of claim 1, wherein heating the substrate further comprises heating the to generate a substrate for amplifying the Raman signal by a factor less than 1,000,000.

5. The method of claim 1, wherein heating the substrate further comprises heating the substrate to a temperature less than 80 degrees Celsius.

6. The method of claim 1, wherein heating further comprises heating the substrate to generate a substrate comprising a network of metallic nanoparticle structures that further comprise hot spots.

7. The method of claim 1, wherein heating the substrate further comprises heating the substrate to a temperature less than 50 degrees Celsius.

8. The method of claim 1, wherein depositing on a substrate further comprises depositing on a substrate comprising paper.

9. The method of claim 1, wherein heating the substrate further comprises heating the substrate for a period of time less than 15 seconds.

10. The method of claim 1, further comprising heating the substrate at a temperature less than 100 degrees Celsius for a period of time less than 30 seconds to generate a substrate comprising a metallic nanoparticle structure comprising an optimum interparticle spacing.

11. An analytical substrate that amplifies Raman signals, the analytical substrate comprising:
   a substrate; and
   at least one metallic nanoparticle structure fabricated by:
      depositing on the substrate a metallic nanoparticle dispersion comprising a metallic nanoparticle population, and
      heating the substrate to a temperature less than 100 degrees Celsius for a period of time less than 30 seconds, wherein the at least one metallic nanoparticle structure amplifies a Raman signal by a factor greater than 10,000.

12. The analytical substrate of claim 11, wherein each metallic nanoparticle of the metallic nanoparticle population comprises an average cross-sectional dimension in a range of about 1 nm to about 100 nm.

13. The analytical substrate of claim 11, wherein each metallic nanoparticle of the metallic nanoparticle population comprises at least one ligand bound to a surface of the nanoparticle, the ligand comprising a heteroatom head group bound to the nanoparticle surface and a tail bound to the heteroatom head group.

14. The analytical substrate of claim 11, wherein the metallic nanoparticle population further comprises particle agglomerate comprised of two or more individual nanoparticles, nanoparticle floc comprised of two or more individual nanoparticles, or any combination thereof.

15. The analytical substrate of claim 14, wherein the ratio, by weight, of the population of individual metallic nanoparticles to particle agglomerate is in the range of from about 1:99 to 99:1.

16. The analytical substrate of claim 14, wherein the ratio, by weight, of the population of individual metallic nanoparticles to particle floc is in the range of from about 1:99 to 99:1.

17. The analytical substrate of claim 14, where the nanoparticle agglomerate has an average cross-sectional dimension in the range of from about 100 nm to about 10000 nm.

18. The analytical substrate of claim 14, wherein the nanoparticle floc has an average cross-sectional dimension in the range of from about 100 nm to about 10000 nm.

19. The analytical substrate of claim 11, wherein the substrate comprises paper.

20. The analytical substrate of claim 11, wherein the at least one metallic nanoparticle structure amplifies the Raman signal by a factor less than 1,000,000.

* * * * *